United States Patent [19]

Servidio et al.

[11] Patent Number: 5,598,838
[45] Date of Patent: Feb. 4, 1997

[54] PRESSURE SUPPORT VENTILATORY ASSIST SYSTEM

[75] Inventors: John L. Servidio; Bruce Beverly, both of Marietta, Ga.

[73] Assignee: Healthdyne Technologies, Inc., Norcross, Ga.

[21] Appl. No.: 419,640

[22] Filed: Apr. 7, 1995

[51] Int. Cl.⁶ ............................................. A61M 16/00
[52] U.S. Cl. ........................... 128/204.23; 128/204.21; 128/204.26
[58] Field of Search ..................... 128/204.18, 204.21, 128/204.23, 204.26, 205.23

[56] References Cited

U.S. PATENT DOCUMENTS

| | | | |
|---|---|---|---|
| 4,036,221 | 7/1977 | Hillsman et al. | 128/204.23 |
| 4,957,107 | 9/1990 | Sipin | 128/204.21 |
| 5,117,819 | 6/1992 | Servidio et al. | 128/204.21 |
| 5,161,525 | 11/1992 | Kimm et al. | 128/204.23 |
| 5,313,937 | 5/1994 | Zdrojkowski | 128/204.23 |

*Primary Examiner*—Aaron J. Lewis
*Attorney, Agent, or Firm*— Jones & Askew

[57] ABSTRACT

A pressure support ventilatory assist device is disclosed. Pressure is provided by a blower which is operated at the minimum speed necessary to achieve the desired inspiration pressure. Pressure regulation is achieved by means of a novel pressure regulator valve, rather than by modulating blower speed, thereby reducing perceptible noise. The flow sensor is removed from its conventional location between the regulator valve and the patient mask to a location upstream of the regulator valve to minimize resistance to patient expiration and to isolate the valve from possible fluids in the tubing. Since the flow sensor in this location cannot sense expiration flows, the device includes circuitry for generating a model of the expiratory waveform based upon the inspiratory waveform. Actual pressure is then modulated to conform to the model waveform.

6 Claims, 16 Drawing Sheets

EXPIRATION MODEL

EXPIRATION MODEL

TRACKING CIRCUIT ZONES

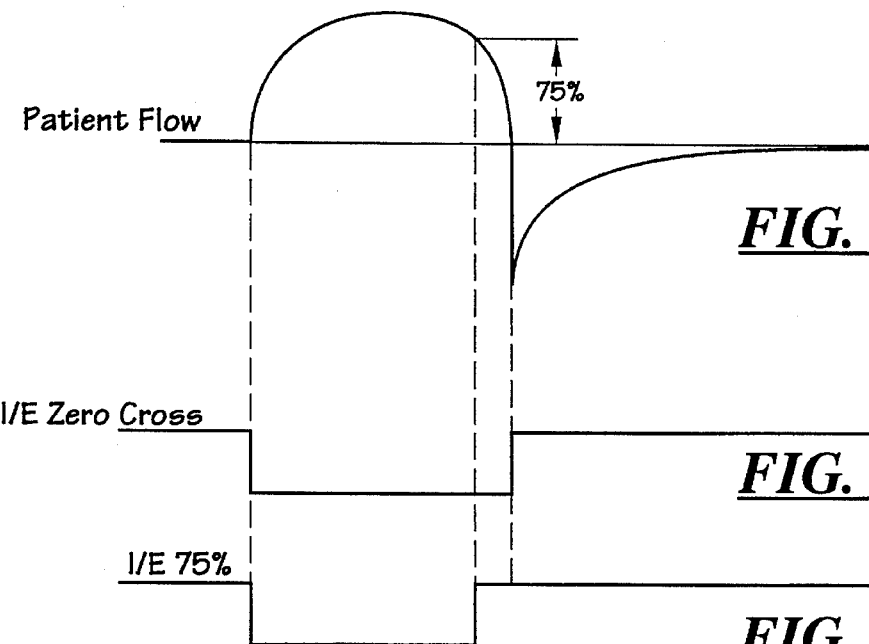
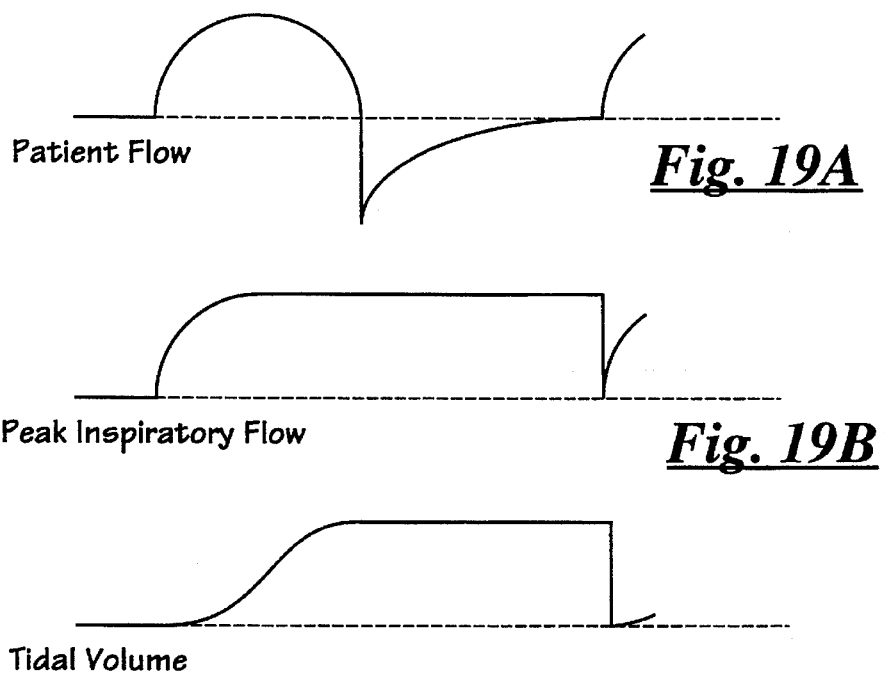

5,598,838

PRESSURE SUPPORT VENTILATORY ASSIST SYSTEM

TECHNICAL FIELD

The present invention relates generally to respiratory devices for medical applications, and relates more specifically to respiratory devices for supplying respiratory gas to a patient under positive pressure.

BACKGROUND OF THE INVENTION

Pressure support devices are well known for supplying pressurized air to a patient by way of a nasal mask. So-called Continuous Positive Airway Pressure ("CPAP") devices have a variety of applications, including assisting respiration and as a treatment for sleep apnea. The positive pressure supplied by the ventilator assists the patient's inhalation, maintains the patency of the patient's airways, and inflates the patient's lungs to a resting volume higher than normal.

An improvement on the basic pressure support device is the bi-level pressure support ventilator, wherein periods of higher pressure are interspersed with periods of lower pressure. The lower pressure facilitates the patient's exhalation, as the patient need not overcome the higher pressure to expel a breath. There have been various approaches to providing bi-level support, including controlling the duration of the high and low pressure intervals by means of a timer, and detecting the patient's inhalation and exhalation, supplying higher pressure during the patient's inhalation and a lower pressure during exhalation.

A problem with some prior art pressure support devices has been that the devices are often perceived by the patient as objectionably noisy. Such ventilators provide positive pressure by means of a blower, with blower speed being rapidly varied to regulate the output pressure to the patient. Since the output pressure varies somewhat with flow, the blower speed was increased or decreased to maintain patient pressure against the disturbance of patient flow. The blower speed variations are exacerbated in those bi-level pressure systems, wherein the blower speed must be varied not only to maintain a constant pressure against the disturbance of patient flow but also to provide the intervals of higher and lower pressure. This rapid variation of the blower speed however, is readily detected by the patient as audible noise.

In addition, some prior art pressure support ventilators operate a blower at maximum speed and lower pressure by exhausting the excess air to atmosphere. This approach avoids the objectionable rapid variation of the blower speed. However, the constant operation of the blower at maximum speed and the venting of large volumes of air to the ambient serve to create an objectionably high noise level.

Thus there is a need for a pressure support device which can maintain a constant pressure against the disturbance of patient flow without the audible noise associated with varying the speed of the blower.

There is a further need for a pressure support device which can supply alternating periods of higher and lower pressures without the audible noise associated with varying the speed of a blower.

There is still another need for a pressure support device which can attain the desired patient pressures without operating its blower at maximum speed and without venting large volumes of air to the ambient.

Another problem associated with certain prior art bi-level pressure support ventilators concerns what is known as "rise time," that is, the time required for the patient pressure to rise from the lower pressure level to the higher pressure level. Rise time figures prominently into patient comfort, as a rise time which is too fast or too slow may not be well tolerated. To complicate matters, a rise time which may be comfortable for one patient may cause discomfort in another patient. For pressure support ventilators which modulate pressure by varying blower speed, it may be difficult to provide meaningful control over rise time.

Thus there is a need for a pressure support ventilator which permits adjustment of rise time to accommodate the comfort of the patient.

Certain prior art bi-level pressure support ventilators which coordinate pressure modulation with the patient's breathing detect inspiration and expiration by means of a flow sensor positioned between the pressure regulator valve and patient. However, locating the flow meter between the valve and patient subjects the flow meter to possible fluids in the patient hose. In addition, the characteristic resistance of the flow meter to a person trying to exhale might be objectionably high.

Thus there is a need for a pressure support ventilator which detects inspiration and expiration of the patient without subjecting the flow meter to possible fluids in the patient hose.

There is also a need for a pressure support ventilator which detects patient inspiration and expiration without a flow meter creating an objectionable resistance to patient exhalation.

SUMMARY OF THE INVENTION

Stated generally, the present invention comprises an improved pressure support ventilatory assist system for providing pressurized air to a patient by way of a nasal mask. The pressure support ventilator can maintain a constant pressure against the disturbance of patient flow and can supply alternating periods of higher and lower pressures without the audible noise associated with varying the speed of the blower. The pressure support ventilator of the present invention permits explicit control of rise time to accommodate the comfort of the patient. Further, the pressure support ventilator can detect inspiration and expiration of the patient without subjecting the flow meter to possible fluids in the patient hose, and without a flow meter positioned so as to create an objectionable resistance to patient exhalation.

Stated somewhat more specifically, the present invention comprises a pressure support ventilatory assist device for supplying pressurized air to a patient by way of a nasal mask. In one operating mode the device detects patient inspiration and expiration and supplies a high patient pressure during patient inhalation and a lower pressure during patient exhalation. The higher pressure assists the patient's inhalation and maintains a patent airway. The lower pressure permits comfortable patient exhalation while still being of sufficient magnitude to inflate the patient's lungs to a resting volume higher than normal and/or to maintain a patent airway.

In one aspect of the present invention, patient inspiration and expiration is detected by a flow sensor which is mounted upstream of the pressure regulating valve. By removing the flow sensor from its conventional location between the patient mask and the regulating valve, the pressure support ventilator of the present invention does not present an objectionable resistance to patient exhalation and does not subject the flow sensor to fluids which may be present in the patient hose.

In another aspect of the present invention, the pressure support ventilator employs a novel servo-controlled pressure regulating valve which affords a high level of control over rise time, that is, the rate at which pressure is raised from the low (expiration) pressure level to the higher inspiration pressure level. The rise time can be adjusted to provide a comfortable pressure increase for any patient.

In yet another aspect of the invention, modulation of the patient pressure in the pressure support ventilator of the present invention is accomplished by maintaining a substantially constant pressure at the inlet side of a pressure control valve and by operating the valve to control pressure at the outlet side. In this manner the speed of the blower is maintained substantially constant, avoiding the rapid speed changes which are readily detectible by the patient as audible noise. Thus not only can pressure be maintained against the disturbance of patient flow without varying the speed of the blower, but also bi-level pressures can be attained without varying the blower speed. The result is a ventilator which is perceived by the patient as quiet.

Thus it is an object of the present invention to provide an improved pressure support ventilator.

It is another object of the present invention to provide a pressure support ventilator which can maintain a constant pressure against the disturbance of patient flow without the audible noise associated with varying the speed of the blower.

Still another object of the present invention is to provide a pressure support ventilator which can supply alternating periods of higher and lower pressures without the audible noise associated with varying the speed of a blower.

It is yet another object of the present invention to provide a pressure support ventilator which permits control of rise time to accommodate the comfort of the patient.

It is a further object of the present invention to provide a pressure support ventilator which detects inspiration and expiration of the patient without subjecting the flow meter to possible fluids in the patient hose.

Yet another object of the present invention is to provide a pressure support ventilator which detects patient inspiration and expiration without a flow meter creating an objectionable resistance to patient exhalation.

Other objects, features, and advantages of the present invention will become apparent upon reading the following specification, when taken in conjunction with the drawings and the appended claims.

BRIEF DESCRIPTION OF THE DRAWINGS

FIG. 15A is a graph showing airflow with an additional leak component added in.

FIG. 17A is a graph showing patient airflow as a function of time; FIG. 17B and FIG. 17C are logic level inspiration/expiration detect signals resulting from the patient airflow of FIG. 17A as input to the CPU board.

FIG. 19A is a graph of patient airflow as a function of time: FIG. 19B is a graph representing the corresponding peak inspiratory flow for the patient breath cycle of FIG. 19A; and FIG. 19C is a graph representing the corresponding tidal volume for the patient breath cycle of FIG. 19A.

DETAILED DESCRIPTION OF THE DISCLOSED EMBODIMENT

Figure 1:
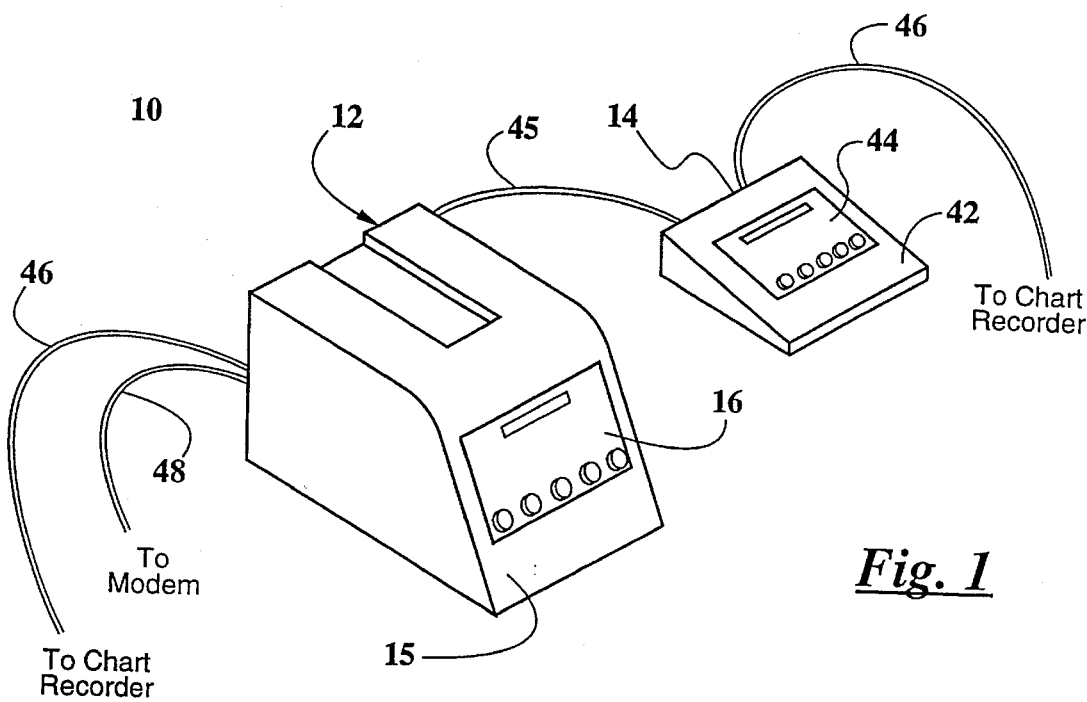
FIG. 1 is a perspective view of a pressure support device according to the present invention.

Referring now to the drawings, in which like numerals indicate like elements throughout the several views, FIG. 1 shows a pressure support ventilator system 10 comprising a main unit 12 and a remote unit 14. The main unit 12 is the pressure source and primary control center for the pressure support ventilator system 10. The main unit 12 includes a front panel 15 to which is mounted an operator control panel 16 by which the pressure support ventilator system 10 is controlled.

Figure 2:
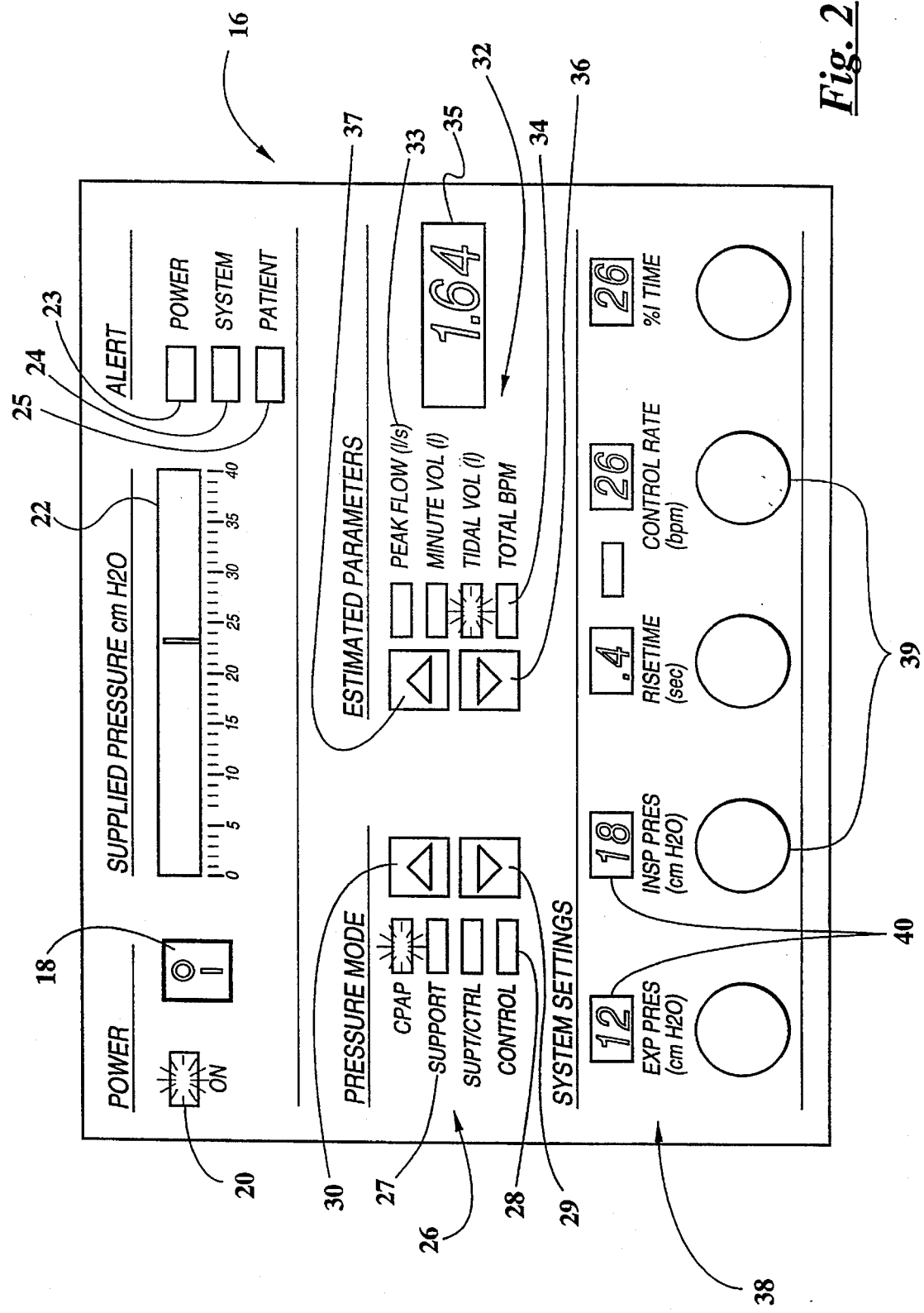
FIG. 2 is a plan view of the control panel of the main unit of the pressure support device of FIG. 1.

FIG. 2 shows the control panel 16. In the upper left hand corner of the control panel 16 is a power on/off switch 18. The power on/off switch 18 is a spring loaded, momentary, normally open switch. A power on light 20 to the left of the power on/off switch 18 illuminates when the power to the main unit 12 is on. To the right of the power on/off switch 18 is a bar gauge 22 which displays the pressure, in centimeters of water, supplied by the pressure support ventilator system 10. The bar gauge 22 displays a range of from 0 to 40 cm H$_2$O. To the right of the bar gauge 22 are three alert lights: a power alert light 23, a system alert light 24, and a patient alert light 25, which illuminate under certain alert conditions, as will be hereinbelow described.

Below the power on/off switch 18 are the pressure mode controls 26. The pressure mode controls 26 permit an operator to set the mode of operation of the pressure support ventilator system 10. The four modes are: CPAP ("Continuous Positive Airway Pressure"), Support, Support/Control, and Control. Indicia 27 corresponding to each of these four modes are imprinted on the face of the control panel 16. A column of indicator lights 28 is positioned beside the indicia 27, one light for each of the various modes of operation; the light 28 corresponding to the selected pressure mode is illuminated during operation. A "down" button 29 cycles through each of the pressure modes, advancing from CPAP toward control. Similarly, an "up" button 30 cycles backward through each of the pressure modes from control toward CPAP. When the first, or CPAP, mode is selected, pressing the "up" button 30 has no effect; the control does not "wrap" around to the last, or control, mode. Similarly, when the last mode is selected, pressing the "down" button 29 has no effect and does not cause the operational mode to wrap around to the first mode.

To the right of the pressure mode controls 26 are the estimated parameters controls 32. The term "estimated" is used because the parameters are being measured indirectly, rather than directly. The estimated parameters are: mean inspiratory flow, defined as the average value of the flow leaving the device less the average value of the predicted leak between the detected beginning and end of inspiration, in liters per second; minute volume, defined as the volume of air inspired by the patient in one minute, in liters; inspired tidal volume, defined as the volume of air leaving the device less the volume of air predicted as leakage between the detected beginning and end of inspiration, in liters; and total breaths per minute. Indicia 33 corresponding to each of the four estimated parameters are imprinted on the face of the control panel 18. The estimated parameters controls 32 include a series of indicator lights 34, one light corresponding to each of the four estimated parameters. The indicator light 34 corresponding to the parameter then being displayed is illuminated. An LED numeric readout 35 exhibits the estimated value of the selected parameter. A "down" button 36 when pressed by the operator cycles forward through the parameters from mean inspiratory flow toward total breaths per minute, while an "up" button 37 cycles backward through the various parameters, from total breaths per minute toward mean inspiratory flow. Depressing the "down" button 35 when the fourth parameter, total breaths per minute, is selected will cause parameter selection to wrap around to the first parameter, means inspiratory flow. Similarly, pressing the "up" button 36 when the first parameter, mean inspiratory volume, is selected will cause parameter selection to wrap to the fourth parameter, total breaths per minute.

At the bottom of the control panel 16 are the system settings controls 38. A row of five rotary knobs 39 is provided for controlling system settings. A corresponding LED display 40 above each of the knobs 39 displays the current setting for that control. The system settings which are controllable by the user are: expiratory pressure, expressed in cm H$_2$O; inspiratory pressure, also expressed in cm H$_2$O; risetime, in seconds; control rate, expressed in breaths per minute; and percent inspiratory time, defined as the duration of the inspiratory time divided by the duration of the entire respiratory period, expressed as a percentage.

The controls actuated by the knobs 39 are rotary incremental encoders. Each rotary step in a clockwise direction causes an increment in the controlled function, while each rotary step in a counter-clockwise direction causes a decrement of the controlled function. While the controls have no stops, i.e., they have infinite travel, the controlled functions do not have an infinite range. When the controlled function would exceed its defined range, further rotation of the control has no effect.

Referring again to FIG. 1, the main unit 12 is most often used as a stand-alone device but can be controlled up to 100 feet away with the optional remote unit 14. The remote unit 14 is used most often in sleep clinics where a theapist in a centralized control room supervises the therapy or diagnostic procedures for nearby patients in sleeping rooms. The remote unit 14 includes an inclined upper surface 42 to which a control panel 44 is mounted. Except for the on/off function, the control panel 44 of the remote 14 duplicates the switches of the control panel 16 of the main unit 12 of the pressure support ventilator 10. When the remote unit 14 is installed, either the main unit 12 or the remote unit 14 can control the pressure delivery settings for the main unit. A single cable 45 connects the main unit 12 to the remote unit 14, handling bi-directional serial communications and delivering power to the remote. The remote 14 may be plugged into the main unit 12 or unplugged during normal operation without adverse effects. Both the control settings of the main unit 12 and the control settings of the remote unit 14 may be enabled simultaneously. The last device to direct a parameter change determines the current setting.

Both main and remote units 12, 14 feature chart recorder outputs 46, providing both output pressure and flow signals. Additionally, the main unit 12 has a modem connection port 48. When a modem is connected to the main unit 12 via the modem port 48, remote control of the pressure support ventilator system 10 is possible via telephone lines. When a modem is connected, control from the remote unit 14 is automatically disabled.

Figure 3:
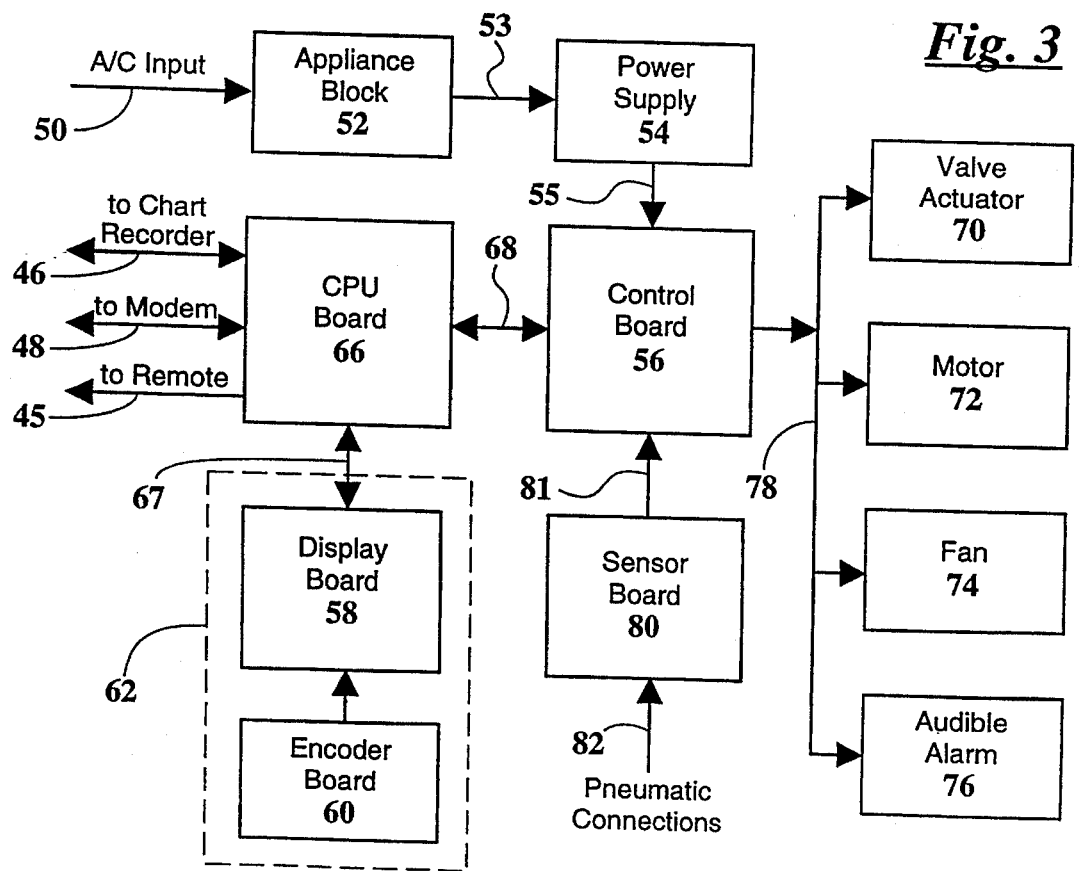
FIG. 3 is a block diagram illustrating the primary electrical components of the main unit of the pressure support device of FIG. 1.

FIG. 3 is a block diagram of the primary electrical components of the main unit 12. External AC power enters the main unit 12 through signal path 50 into a rear-panel appliance block 52, which contains the main fuse. The appliance block 52 sources power by a signal path 53 to a main power supply 54. The power supply 54 generates +24 V as the main DC rail of the device. It sends +24 V by a signal path 55 to a control board 56, which serves as the DC power distribution point for the internal components.

Still referring to FIG. 3, a display board 58 and encoder board 60 form the electrical front panel operator interface 62. The operator interface 62 includes the control panel 16 with its displays and switches and the associated drive/interface circuitry. The display board 58 is mounted to the interior surface of the front panel 15 of the main unit 12. The encoder board 60 fastens to the rear of the display board 58. The rotary incremental encoders actuated by the knobs 39 of the control panel 16 are mounted to the encoder board 60, and rotary shafts of the encoders are received through corresponding through-holes in the display board 28. The encoder board 60 detects the settings of the knobs 39 and transmits the information to the display board 58.

The display board 58 is connected to a CPU board 66 by way of signal path 67 comprising a short 50-pin ribbon cable. The cable 45 to the remote 14, the chart recorder output 46, and the modem port 48 are also connected to the CPU board 66. The primary role of the CPU board 66 is to use the operator input information from the display and encoder boards 58, 60 to create a device output pressure profile, as will be more fully explained below. The CPU board 66 sends this output pressure information to the control board 56 by way of a signal path 68. In turn, the control board 56 drives the electromechanical devices that actually deliver the pressure. These devices include a valve actuator 70, a motor 72, a fan 74, and an audible alarm 76, all of which are connected to the control board 56 by a suitable wiring harness 78. The motor 72 drives a centrifugal blower that develops the pressure source. The valve actuator 70 is part of a valve assembly, more fully discussed below, that operates as a variable restrictor to regulate the pressure delivered from the blower. The fan 74 directs air through the housing of the main unit 12 to cool the power supply 54. The audible alarm 76 alerts the operator in conjunction with user alert conditions, as will be explained below.

The control board 56 is connected to a sensor board 80 connect via a signal path 81 consisting of a small ribbon cable. The sensor board 80 receives pneumatic connections by way of a suitable input 82 to detect required pressure and flow data. The sensor board 80 further contains transducers that convert air pressure and air flow into electrical signals and sends these signals to the control board 56 via the signal path 81. Using this information, the control board 56 compares the desired pressure from the CPU board 66 to the actual pressure from the sensor board 80 and uses closed loop control to command the valve actuator 70 and motor 72. In this way the actual pressure delivered follows the desired pressure settings on the system settings controls 38 of the control panel 16. The control board 56 also handles some flow signal processing. In certain operational modes it coordinates its pressure fluctuations with the patient's own respiration demands to provide respiratory support just when it is needed.

The operation of the encoder board 60 will now be explained. As previously discussed, the control panel 16 on the front panel 15 of the main unit 12 features five control knobs 39. By turning these knobs 39 a user may adjust desired pressure waveform settings. The goal is to have analog-like controls which are intuitive to use, but with digital readouts that allow precise settings that do not drift over time. In hospital environments it is desirable to have parallel access to any of the main controls (without having to scroll through menus, etc.). Moreover, the remote unit 14 must be able to control the pressure support ventilator 10 while the control panel 16 of the main unit 12 is still enabled, without conflict. To meet these requirements, the disclosed embodiment uses low-cost rotary resistive digital encoders, made by Bourns.

Each encoder turns infinitely in either clockwise or counter-clockwise direction. In the disclosed embodiment the encoder has mechanical detents, twelve per revolution. There are three electrical connections per encoder: channel A, channel B, and common. Inside the encoder is a resistive disk that alternately connects/disconnects channel A and channel B with the common pin. When the encoder disk rotates, the signals on channel A and B generate an industry-standard sequence. From it, decoding circuitry can tell the direction of rotation and count each increment (or phase) of rotation. In the pressure support ventilator 10, the microcontroller on the CPU board 66 reads the encoder signals on an interrupt scan basis. The relationship between encoder position and its associated control parameter is completely software determined. At the end of each parameter range, a software limit takes effect. Further encoder turns toward out-of-range are ignored. Turns back toward the operational range take effect immediately. In some pressure support ventilator modes, a particular control parameter may not be applicable. In those modes, the software simply ignores those encoders.

The operation of the display board 58 will now be discussed. The display board 58 contains all of the numeric displays and other visible indicators of the control panel 16 required as part of the operator interface. The same printed circuit board is used in the main and remote versions, but the boards are populated slightly differently. The chief difference is that the main version has a power on/off switch 18 while the remote version does not. The display board 58 includes the four momentary-type pushbutton switches 29, 30, 36, and 37 for the mode up/down and patient data up/down features. The encoder channel signals from the encoder board 60 are communicated to the display board 58. The display board 58 adds Schmitt trigger inverters on each of the lines, and passes the outputs on to the CPU board 66 as data inputs.

The operation of the CPU board 66 will now be discussed with reference to FIG. 4. The primary role of the CPU board 66 in the operation of the pressure support ventilator system 10 is to generate a desired command pressure waveform or profile. As will be more fully explained below, the control board 56 will then match the actual pressure support ventilator output pressure to the command pressure waveform generated by the CPU board 66. The CPU board 66 also serves as an integral part of the control panel 16 of the operator interface. Through the control panel 16, the operator can tailor the pressure waveform in terms of levels, duty cycles, timing, and so on. It will be appreciated that in the version of the CPU board which resides in the remote unit 14, the interface to the control board is not populated. It therefore serves as an operator interface and communicates to the main unit 12 via a serial interface.

Figure 4:
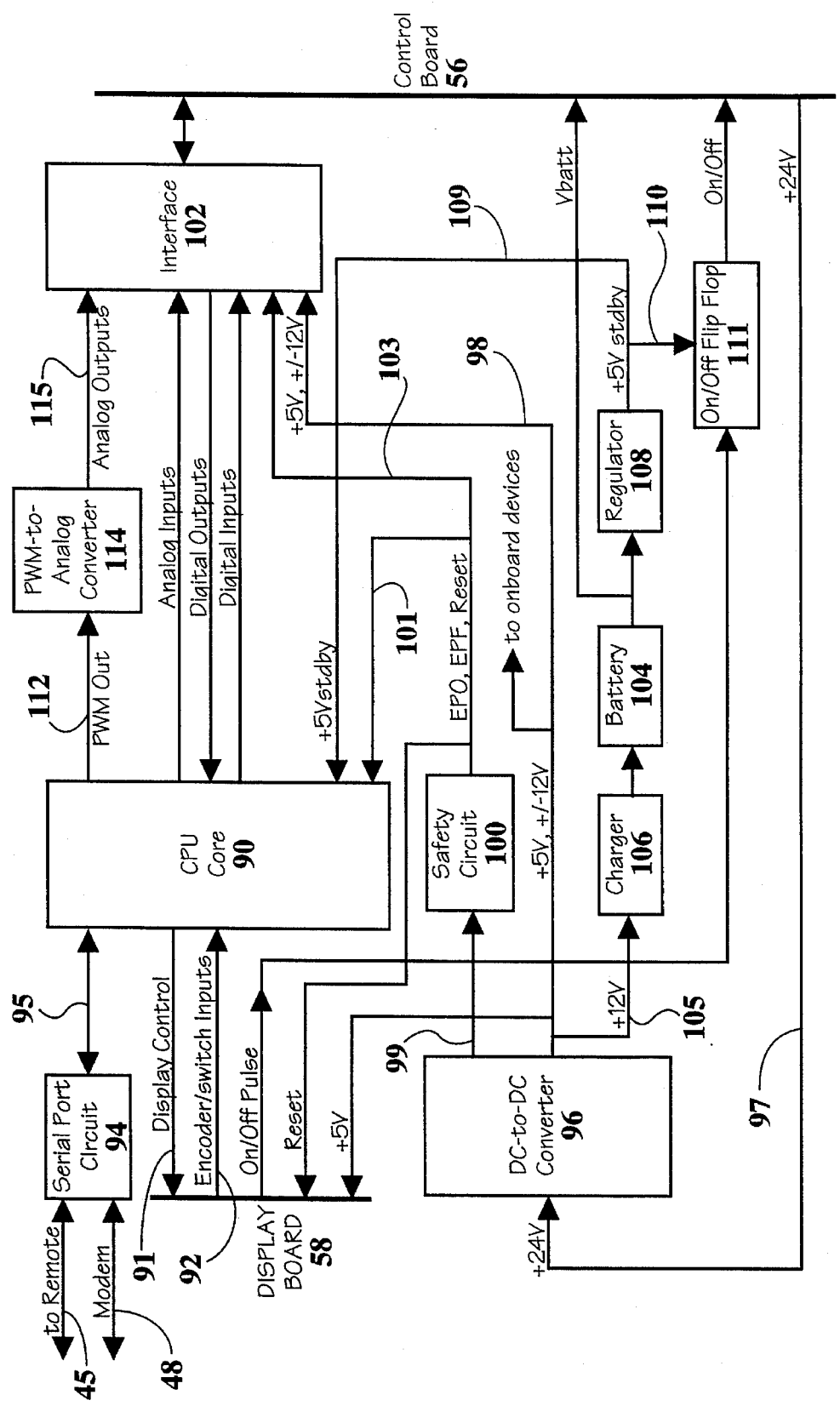
FIG. 4 is a block diagram of a CPU board of the pressure support ventilator system of FIG. 1.

As can be seen in FIG. 4, the CPU board 66 includes a CPU core 90 which comprises an Intel 80C196 microcontroller and its peripheral devices. A parallel interface comprising signal paths 91 and 92 connects the CPU core 90 to the display board 58. Using a periodic scan, the CPU core 90 reads the encoders from the display board 58 and updates the displays on the display board. The display is a multiplexed arrangement that requires constant refresh writes from the CPU.

The CPU board 66 further includes a serial port circuit 94 consisting of a differential transceiver RS422 interface for communications between the main unit 12 and the remote unit 14 and transceivers for RS232 communications to a modem device. The serial port circuit 94 communicates with the CPU core 90 by way of a signal path 95. There is only one serial port in the CPU core 90, so the two receive lines switch between the remote and modem devices.

Still referring to FIG. 4, a DC-to-DC converter 96 on the CPU board 66 accepts +24 V from the control board 56 by way of a signal path 97 and generates logic and analog rails (+5 V, +/−12 V) 98. By way of a signal path 99, a safety circuit 100 monitors the power supply from the DC-to-DC converter 96 and generates powerup reset, early power fail ("EPF"), and early power on ("EPO") signals. EPF warns the CPU that a power failure is eminent, so it may have an orderly shutdown. EPO announces a powerup, so that a power fail alarm in the alarm circuit may be reset. Powerup reset, EPF, and EPO signals are transmitted from the safety circuit 100 to the CPU core 90 by a signal path 101 and to a generic interface 102 to the control board 56 by way of a signal path 103.

The CPU board 66 also contains a rechargeable 9 V NiCad battery 104. +12 V is transmitted by a signal path 105 from the converter 96 to a charger 106, which constantly trickle charges the battery 104 by way of a signal path 107. A special low-standby current regulator 108 connected to the battery by a signal path 109 generates +5 V stdby, for the purpose of memory retention of RAM contents. By way of a connection 110, the regulator 108 also powers a flip flop 111 which stores the on-off state of the unit.

The CPU core 90 uses pulse-width-modulation ("PWM") outputs for scalar outputs. Pulse width output from the CPU core 90 is transmitted by a signal path 112 to an onboard PWM converter 114. The PWM converter 114 converts the pulse width output from the CPU core 90 into analog voltages which are passed to the interface 102 to the control board 56 by way of a signal path 115. Analog inputs from the display board 58 are transmitted from the interface 102 to the CPU core 90 by way of a signal path 116. Similarly, digital inputs and outputs are transmitted between the CPU core 90 and the interface 102 to the control board 56 by way of signal paths 117, 118.

The operation of the control board 56 will now be discussed with reference to FIG. 5. The primary role of the control board 56 in the operation of the pressure support ventilator system 10 is to control the air pressure delivered to the patient. In general terms, the control board 56 receives the waveform generator output from the CPU board 66 as the desired pressure profile The control board 56 also receives actual pressure and flow data from the sensor board 80. The control board 56 then compares the desired pressure with the actual pressure and continuously regulates power to the regulator valve actuator 70 and blower motor 72 (FIG. 3) in such a way that the delivered pressure follows the commanded pressure. The control board 56 also controls auxiliary functions including flow signal processing, alarm logic circuitry, and power on/off control.

More specifically, the desired pressure output from the CPU board 66 is received via a signal path 120 and transmitted to a valve control 122. The actual pressure from the sensor board 80 is transmitted to the valve control 122 by way of a signal path 123. The valve control 122 compares the pressures and sends an output signal via a signal path 124 to an amplifier 125, which amplifies the output signal and transmits the amplified output signal via a signal path 126 to the valve actuator 70 (see, e.g., FIG. 3).

Figure 5:
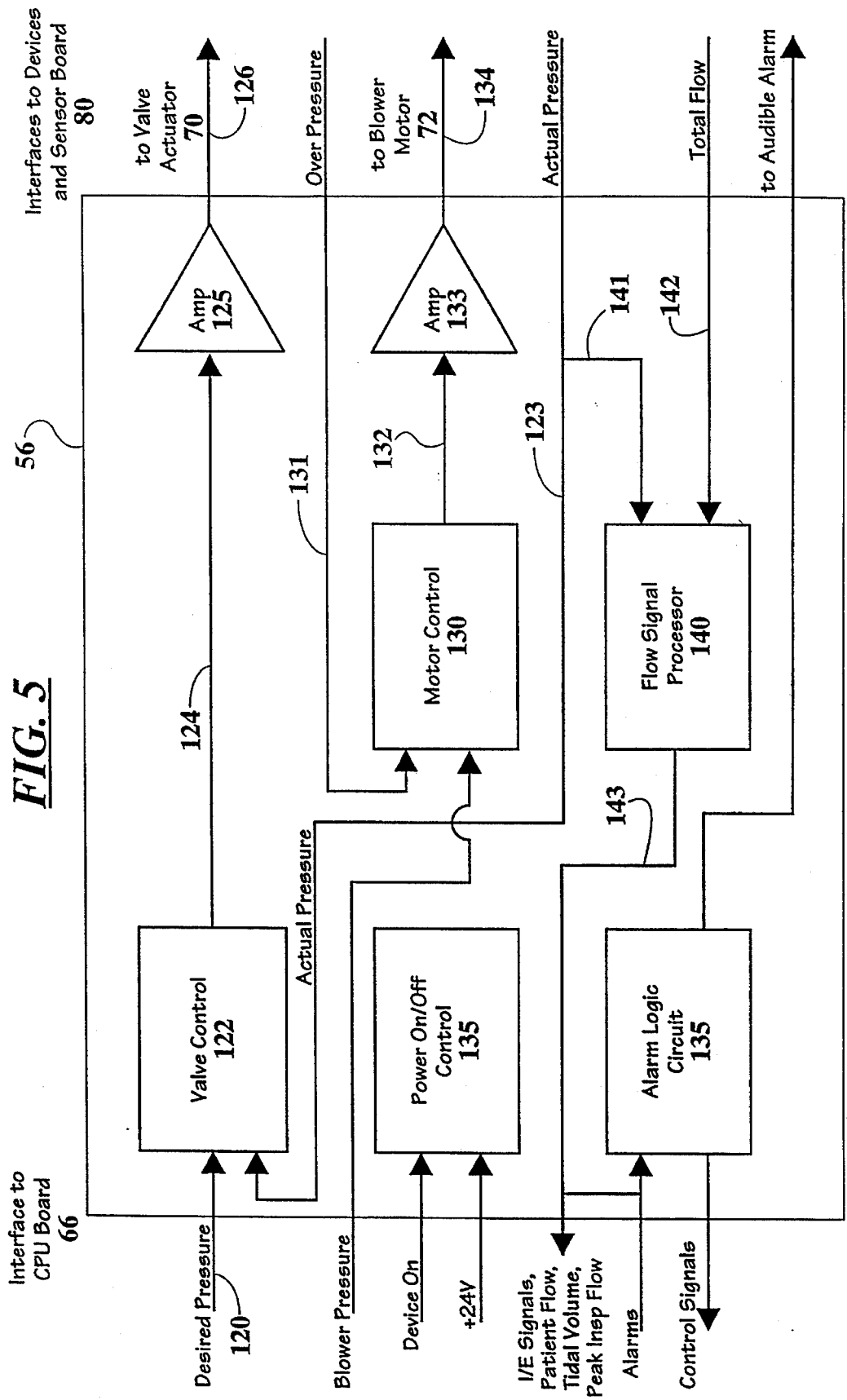
FIG. 5 is a block diagram of a control board of the pressure support ventilator system of FIG. 1.

As is further shown in FIG. 5, a blower pressure output from the CPU board 66 is received at the control board 56 by way of a signal path 128 and transmitted to a motor control 130. The over pressure from the sensor board 80 is transmitted to the motor control 130 by way of signal path 131. The motor control 130 compares the over pressure to the blower pressure and sends an output signal via signal path 132 to an amplifier 133, which amplifies the output signal and transmits the amplified signal via signal path 134 to the blower motor 72 (see, e.g., FIG. 3).

Referring once again to FIG. 5, the control board 56 further comprises an alarm logic circuit 135. While the alarm system actually encompasses components on several circuit boards, the alarm logic circuit 135 resides on the control board 56. The pressure support ventilator main unit 12 features both audible and visible alarms for the three conditions: power fail alarm, patient (disconnect) alarm, and system alarm. A power fail alarm occurs after a loss of external power while the device is on. A patient alarm may occur during normal operation if high flows persist, indicating the patient's mask is off. A system alarm may occur during normal operation at the onset of a pressure error or other error condition detected by the CPU. The alert LEDs 23–25 on the control panel 16 (see FIG. 2) are mounted on the display board 58 and are illuminated during the appropriate alert condition, and the internal audible alarm 76 sounds to coincide with any of the three alarms.

The control panel 44 of the remote unit 14 has three alarm LEDs also, but they illuminate in unison to indicate a general alarm condition. Since the remote unit 14 has no audible alarm, its three LEDs flash on and off during an alarm condition to attract attention. To learn which of the three alarm conditions exist, the operator must go to the main unit 12 and observe its control panel 16.

The alarm logic block 135 accepts inputs to generate the three different alarms. The sensor board 80 outputs a total flow signal, which is processed on the control board 56. Part of that processing includes the detection of a patient disconnect, generally related to high flows for more than twenty seconds. The sensor board 80 also provides a high pressure signal, generated from an over-pressure switch monitoring blower pressure. The alarm logic block 135 detects an unintended (by the user) loss of power, and generates a power fail alarm. The CPU core 90 of the CPU board 66 compares the desired pressure to the actual pressure and generates a signal press error when a discrepancy occurs. This error may be disqualified by a flow limit condition on the control board 56, however. The CPU core 90 may also generate a CPU alarm in the case of a diagnostic failure or other internal error. Any of the three signals—press error, CPU alarm, or high pressure—will cause the alarm logic block 135 to output a system alarm. The CPU core 90 monitors the patient alarm and system alarm lines, which may be asserted from conditions not otherwise visible to the CPU. In this way the CPU may report via a modem device any existing errors.

Still referring to FIG. 5, the control board 56 further includes a flow signal processor 140. An output signal from the sensor board 80 representing actual pressure is forwarded by way of a signal path 141 to the flow signal processor. Another output signal from the sensor board 80, this one representing total flow, is transmitted to the flow signal processor 140 via signal path 142. The flow signal processor 140 processes these signals and generates output signals corresponding to inspiration/expiration, patient flow, tidal volume, and peak inspiration flow via signal path 143 to the CPU board 66.

The basic task of the flow signal processor 140 is to generate inspiration/expiration (I/E) signals to help the pressure waveform generator of the CPU board 66 in its timing of pressure changes. Additionally, the flow signal processor 140 extracts information from the total flow signal to deliver to the CPU board 66 the following signals: patient flow, peak inspiratory flow, and tidal volume.

Finally, the diagram of the control board 56 shown in FIG. 5 includes a power on/off control 145. The power on/off control 145

Figure 6:
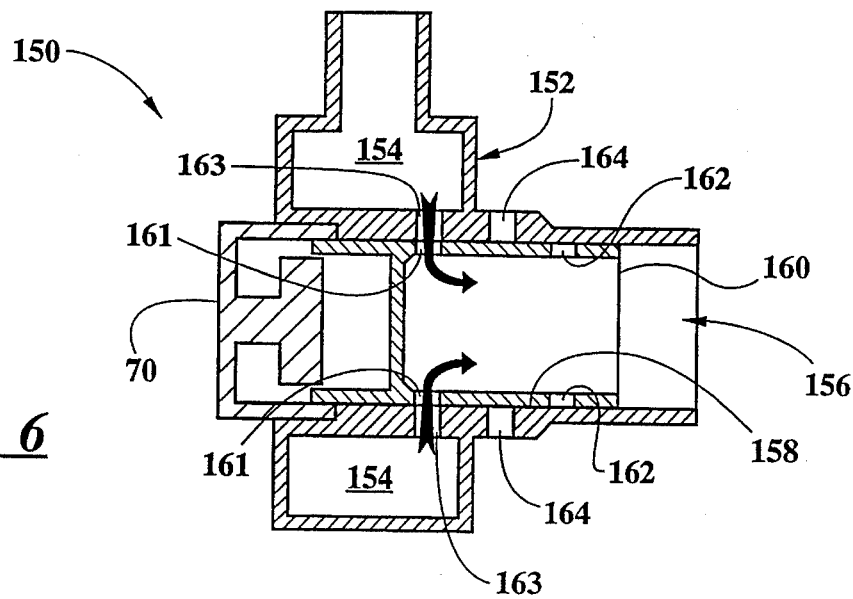
FIG. 6 is a cross-section view of a valve which regulates pressure in the pressure support device of FIG. 1, with the valve in an "intake" configuration.
Figure 7:
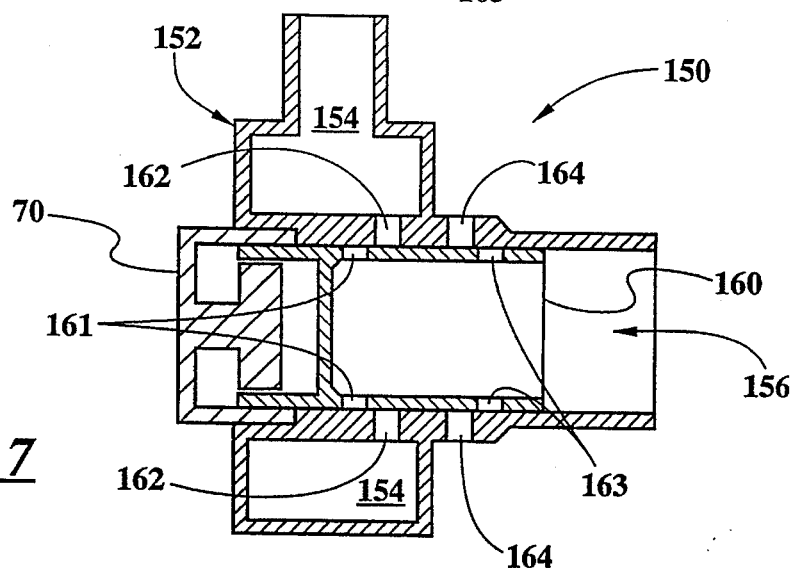
FIG. 7 is a cross-section view of the valve of FIG. 6 with the valve in a "neutral" configuration.
Figure 8:
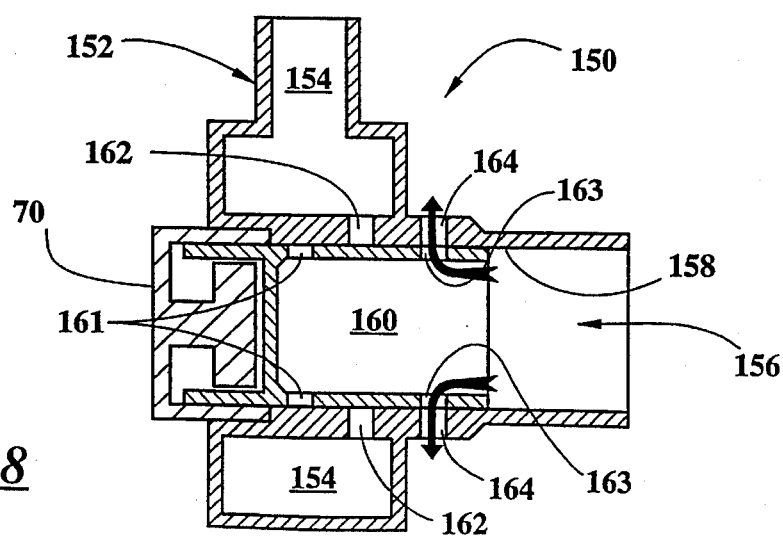
FIG. 8 is a cross-section view of the valve of FIG. 6 with the valve in an "exhaust" configuration.

FIGS. 6–8 illustrate a valve 150 which plays a major part in controlling and modulating pressure within the pressure support ventilator system 10. The valve 150 comprises a housing 152 having an inlet passage 154 and an outlet passage 156. The inlet passage 154 is connected to a pressure source, while the outlet passage 156 is connected via suitable tubing to a patient mask. The housing 152 further comprises a round bore 158, within which a closed-end, hollow piston 160 is slidably mounted. Two rows of circumferential slots or ports 161, 162 are cut in the piston 160. Two like rows of circumferential ports 163, 164 are formed in the housing 152. The ports 161 in the piston 160 and the ports 163 in the housing 152 comprise intake ports, and the ports 162 in the piston 160 and the row of ports 164 in the housing 152 comprise exhaust ports.

A voice-coil type electromagnetic actuator, previously numbered 70 (FIG. 3) is mounted to the housing 152 and exerts a force against the end of the piston 160. The actuator 70 generates a force which is proportional to the amount of electric current passed through it. Also, the force can be exerted almost independent of the displacement of the piston 160. It will be appreciated that other suitable means of generating a force may be used.

In FIG. 6 the valve 150 is in its intake position. The piston 160 is displaced to the right within its bore 158. In this position the intake ports 161 in the piston 160 are aligned with the intake ports 163 in the housing 152. The inlet passage 154 is thereby in fluid communication with the outlet passage 156. Thus a fluid under pressure in the inlet passage 154 will pass through the intake ports 161, 163 and exit the valve 150 through the outlet passage 156.

In FIG. 7 the valve 150 is in a neutral position. The piston 160 is displaced part way toward the left within its bore 158. In this position neither of the sets of ports 161, 162 in the piston 160 are aligned with the ports 163, 164 in the housing 152. The inlet passage 154 and outlet passage 156 are thereby both closed, and fluids under pressure in either the inlet passage 154 or the outlet passage 156 will remain within that passage.

FIG. 8 illustrates the valve 150 is in its exhaust position. The piston 160 is displaced all the way to the left within its bore 158. In this position the exhaust ports 162 in the piston 160 are aligned with the exhuast ports 164 in the housing 152. The outlet passage 156 is thereby in fluid communication with the ambient, such that a fluid under pressure in the outlet passage 154 will pass through the exhaust ports 162, 164 and exit the valve 150.

Regulation of pressure by the valve 150 is effected by varying the forces acting on the piston 160 that cause it to slide in the housing bore 158. Fluid pressure inside the piston 160 is the same everywhere and is also the same as the outlet pressure. The net force $F_1$ on the piston 160 due to the pressure in the outlet passage 156 is equal to the pressure P times the area A of the piston (i.e., $\pi r^2$). The actuator 70 can be operated to exert an oppositely directed force $F_2$ of equal magnitude such that the net force on the piston 160 is made equal to zero. In that case, the piston 160 does not move. In the case of such a force balance, $F_1=F_2$, or $F_2=PA$. Upon rearranging we have that $P=F_2/A$. Since the area, A, is a constant, the pressure is a linear function of $F_2$. By externally applying $F_2$ and holding it constant, P can be held constant or regulated.

If the pressure within the outlet passage 156 increases, then the force $F_1$ increases and force balance does not hold. Now $F_1>F_2$ and the net force on the piston 160 causes it to move. The movement is in a direction to align, and thereby to open, the exhaust ports 162, 164. As the exhaust ports 162, 164 open, fluid is exhausted from the outlet passage 156, causing the pressure within the outlet passage to drop. The piston 160 then begins to displace back toward the right, as shown in FIGS. 6–8, such that the exhaust ports 162, 164 start to close. When the pressure within the outlet passage 156 has dropped to the regulated value, the force balance is again operative, and the ports will be open to whatever extent is necessary to cause that force balance.

Likewise, if the pressure within the outlet passage 156 decreases, the force $F_1$ decreases, and the force balance does not hold. Now $F_2>F_1$, and the net force on the piston 160 causes it to move toward the fight as shown in FIGS. 6–8. The piston 160 is displaced until the inlet ports 161, 163 on the piston and housing 150, respectively, are aligned. As the inlet ports 161, 163 open, fluid is supplied to the load causing the pressure within the outlet passage 156 to rise. As the pressure within the outlet passage 156 begins to rise, the force $F_1$ exerted against the piston 160 also rises, displacing the piston such that the inlet ports 161, 163 start to close. And when the pressure has increased to the regulated value, force balance is again restored, and the ports will be open to whatever extent is necessary to maintain that force balance.

The piston 160 will move to uncover either the exhaust or inlet ports as required to regulate the outlet pressure such that $P=F_1/A$. The regulating valve 150, therefore, sources or exhausts as required to regulate the outlet pressure within the outlet passage 156.

The fluid for which the valve 150 was designed is air. However, the principles are equally applicable to any other fluid. The ports described are a single set, both for inlet and exhaust; however, any number of sets of ports can be used. For example, to attain the same port areas, two sets of ports could be used with the dimension in the direction of movement halved. Thus the displacement of the piston can be designed independent of port area. Other modifications will be apparent to those skilled in the art.

The valve 150 exhibits very fast response. Since the valve 150 of the disclosed embodiment uses an electromagnetic actuator 70, it is readily modified electrically to change its response. The concept has been expanded to modulate the force $F_2$ that sets the output pressure, with a signal generated by the velocity of the piston 160. When modified in this manner, the response of the valve 150 can be slowed down or damped. This characteristic is especially useful when the valve 150 is required to rapidly change pressure, as the damping adds stability and prevents the piston 160 from "overshooting." Other types of damping means can be used, in lieu of or in conjunction with modulation of the electromagnetic actuator, including but not limited to a pneumatic dash pot.

A further feature of the valve 150 is the capability to transduce the output pressure to an electrical signal. That signal can then be compared to a reference electrical signal that represents the desired pressure. The overall system is then an electrical servo system that controls a fluidic servo system. When the electrical servo system is employed, the basic regulating properties of the force balance system are enhanced. The overall system can be made insensitive to the orientation of the device (gravity effects) and to the undesired forces acting on the piston due to the physical system being moved or jarred.

Figure 9:
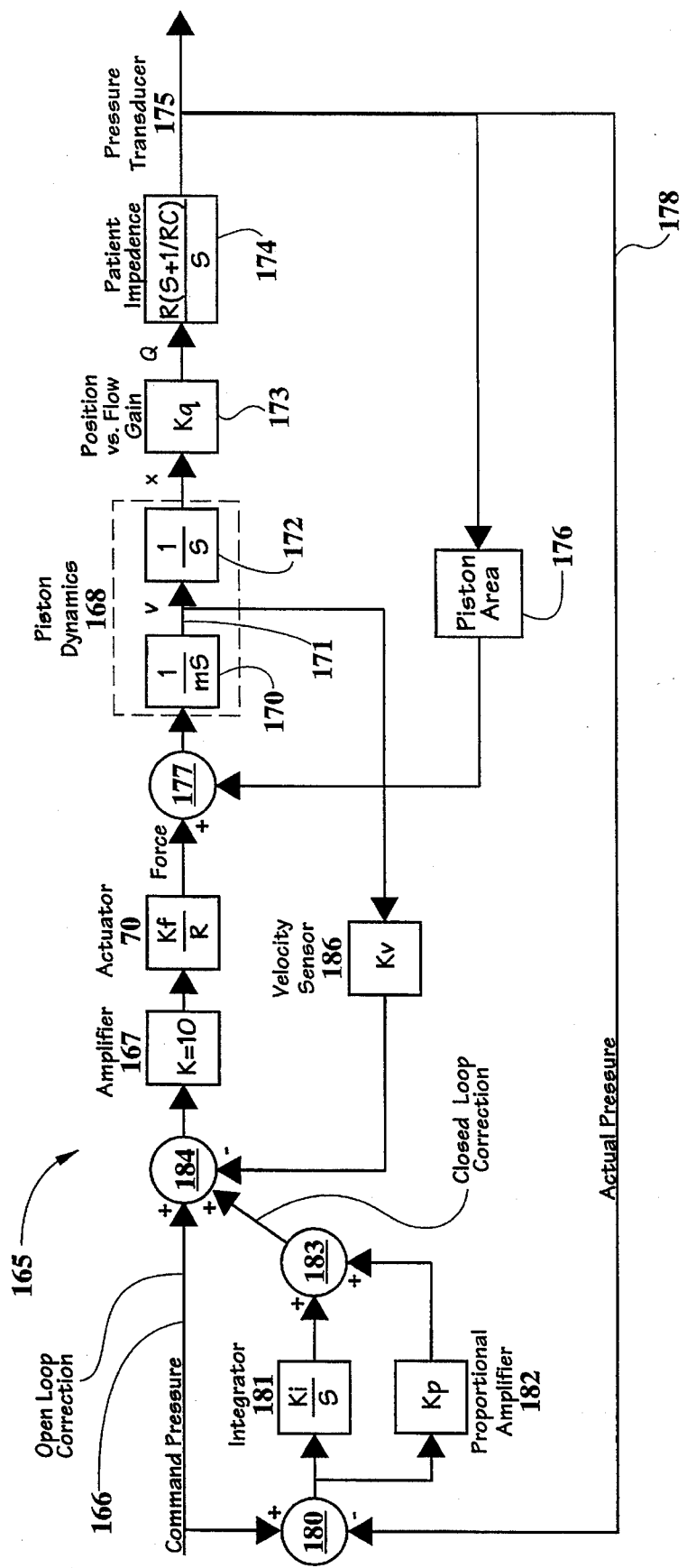
FIG. 9 is a block diagram of a valve control feedback control loop employed by the pressure support device of the present invention.

The operation of the valve 150 is controlled by a valve control loop 165. A dynamic block diagram of the valve control loop 165, including the valve 150 and the patient, is shown in FIG. 9. A signal corresponding to a command pressure is input into the control loop 165 by way of a signal path 166. Referring first only to the open loop portion of the control loop 165, the command pressure signal is amplified by an amplifier 167 and passed on to the valve actuator 70, which converts the signal into a force. The force is exerted against the piston 160 of the valve 150. The dynamics of the piston 160 are represented by the objects inside the dashed line 168. In the block 170 the force is divided by the mass m of the piston 160, resulting in an acceleration value; this acceleration value is integrated to determine a velocity v of the piston 160. A signal corresponding to the velocity is output along signal path 171. In the next block 172 the velocity v of the piston 160 is again integrated to determine a displacement x of the piston 160 with respect to the valve housing 152. The position of the piston 160 with respect to the valve housing 152 determines the extent to which the ports 161, 162 in the piston 160 are aligned with the ports 163, 164 of the valve housing 152 (see FIGS. 6–8). The airflow Q through the valve 152 is a consequence of the valve's displacement; the block 173 labeled "Position vs. Flow Gain," determines the airflow based upon the displacement of the piston 160.

The block 174 in FIG. 9 represents the patient impedance, represented by the equation $R(S+1/RC)/S$, where R is the patient resistance to airflow (e.g. the patient's airways) and C is the patient's compliance, which is a consequence of the elasticity of the patient's lungs. The airflow Q against the patient's impedance results in a patient pressure.

The valve control loop 165 makes use of the properties of the valve 150 as an open loop pressure regulator. The electromagnetic valve actuator 70 generates a force that is linearly proportional to the current through its windings. The valve 150 regulates pressure to maintain a force balance with the actuator 70. The force exerted by the valve 150 is equal to the area of the piston 160 times the pressure, as measured by the transducer 175. This force is represented by the block 176 and is subtracted from the command pressure at node 177. So, for a given voltage applied to the fixed resistance in the coil of the actuator 70, an essentially constant current is generated in the coil, and hence a fixed pressure is exerted by the actuator 70. The fixed voltage is derived within the electronics as a scaled version of the command pressure signal.

If the piston 160 of the valve 150 is moving, which is the normal case during breathing, the current is not strictly equal to the voltage divided by the resistance. The pressure generated is therefore not exactly equal to the desired pressure. To account for this, the actual pressure is measured by the pressure transducer 175, and a signal corresponding to the measured pressure is transmitted along signal path 178 to a node 180 where it is subtracted from the command pressure. This is a standard servo loop error signal. The error signal is processed through an integrator 181 and a proportional amplifier 182. The sum of these two signals is added at node 183, and the summed signal is added at node 184 to the command pressure signal. This corrected signal is then applied to the coil of the valve actuator 70.

Since the open loop control is very close to ideal in the steady state, the closed loop portion of the control functions mainly to control the transient response of the valve regulator. Additionally, the integrator 181 in the closed loop portion of the control serves to null out any steady state errors. That is, with the open loop control the actual pressure is very close but not exactly equal to the desired pressure. The closed loop portion of the control reduces this finite error almost to zero.

Because the valve/patient combination is of at least the third order, it is subject to instability (with the integrator in the control loop, the entire loop is at least of fourth order). To control the transient response and to maintain stability, rate feedback in the form of velocity sensing is implemented in the control loop. The velocity of the piston 160 is measured with a moving magnet transducer which is mounted rigidly to the piston. In FIG. 9 the transducer is represented by the block 186 labeled "velocity sensor." The signal from this transducer 186 is linearly proportional to the velocity of the piston 160. This signal is amplified and then subtracted from the drive signal at node 184. The result is enhancement of stability.

Note that the velocity signal is not subtracted from the error signal as is often done in classic feedback systems. Since the piston 160 of the valve 150 is nearly always moving, subtracting a velocity term from the error signal would indicate to the closed portion of the control that the error was less than it actually was. By subtracting the velocity term from the drive signal at node 184, the loop is still damped, but the error signal remains the true error, and the integrator can function to apply corrective signals during movements of the piston 160.

Figure 10:
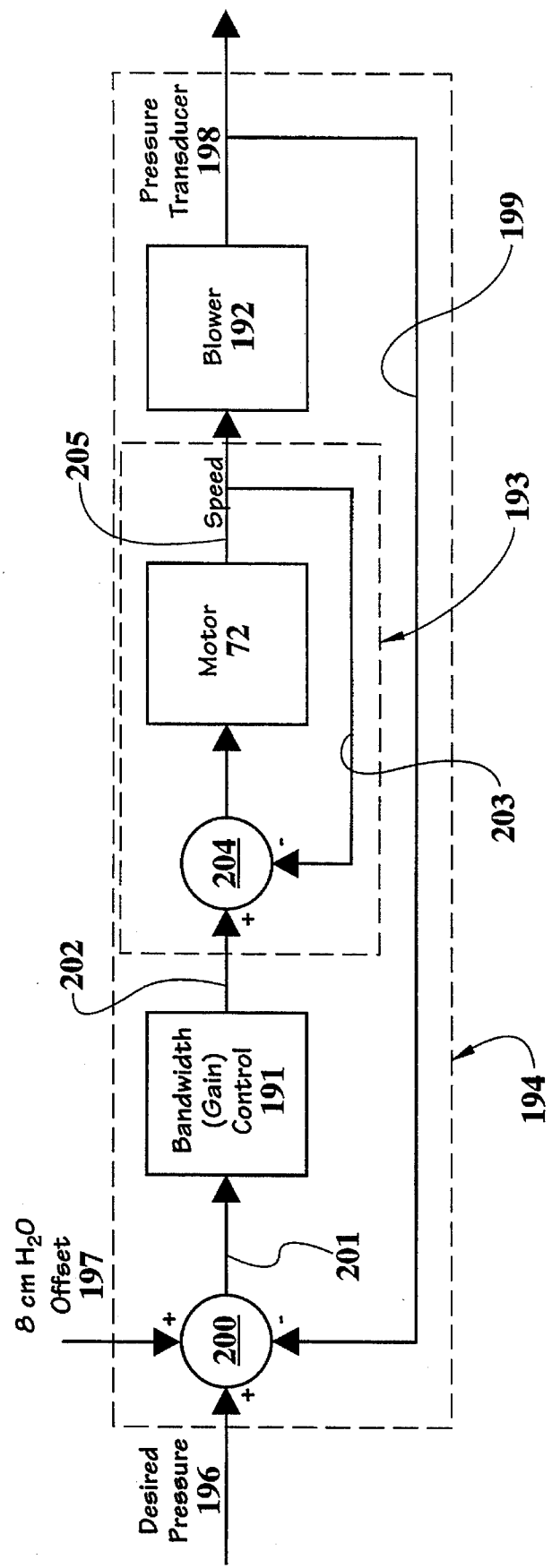
FIG. 10 is a block diagram of a feedback control loop employed by the pressure support device of the present invention to control the speed of the motor driving the blower.

Operation of the motor control 130 will now be further discussed by reference to FIG. 10, which is a diagram of a feedback loop 190 used by the motor control 130 to control the blower motor, which has previously been assigned the reference numeral 72 in conjunction with the discussion of FIG. 3. Stated generally, the feedback loop 190 of FIG. 10 includes the following components: a bandwidth (gain) control 191, the blower motor 72, and a centrifugal blower 192 which is driven by the motor 72. The feedback loop 190 actually comprises two interrelated loops: an inner or "motor speed" loop 193, and an outer or "pressure" loop 194.

The output pressure of the blower 192 is important because the blower is the source of pressurized air for the patient air delivery of the device. The blower pressure must be high enough to meet the output pressure requirements for the patient as well as the pressure drops that exist in the flow sensor, the valve, and misc. losses in tubing, etc. The output pressure must not be too high because higher pressures, since they require higher blower speeds, result in higher noise. The function of the motor control 130 is to attain the highest pressure which will be needed by the system at any point during its operation. To avoid rapid increases or decreases in the speed of the blower motor 72, which are perceived by the patient as audible noise, the motor control 130 is not used to modulate the pressure in accordance with the patient's inspiration and expiration; that modulation is controlled by the valve control 122 in conjunction with the valve 150. The motor control 130 thus operates simply to provide the input pressure to the valve 150, and the valve control 122 operates to modulate pressure to the patient, as will be more fully described below.

In the motor control feedback loop 190, the object is to operate the blower 192 at a speed sufficient to achieve a predetermined pressure which is just high enough to meet the inspiratory pressure demands of the patient and the pressure losses in the system. A desired pressure, which is the inspiration pressure as set by the system controls 38 on the control panel 16, is input into the loop at 196. The system suffers pressure losses in the valve and the flow sensor of about 3 cm $H_2O$ each (or 6 cm $H_2O$ total) at peak flow. Additional pressure losses corresponding to approximately 2 cm $H_2O$ result from losses in tubing. Accordingly, to account for these losses an offset pressure of +8 cm $H_2O$ is input into the system at 197. The actual pressure generated by the blower is measured by a pressure transducer 198, and a signal corresponding to the actual pressure is transmitted along signal path 199. At node 200 the desired pressure and the offset pressure are added, and the actual pressure is subtracted. An output signal corresponding to the summed pressures is then output via a signal path 201.

The signal is then processed by the bandwidth (gain) control 191 and the processed signal, corresponding to the motor speed necessary to achieve the desired pressure, is output along a signal path 202. In the motor speed loop 193, a signal corresponding to the actual speed of the motor is transmitted along signal path 203 to node 204, where the actual motor speed is subtracted from the desired motor speed. A corrected output signal is then transmitted along signal path 205 to the blower motor 72. In response to this input the blower motor 72 drives the blower 192.

The blower motor control loop 190 uses as its inputs the inspiratory pressure level and the actual blower output pressure level. The output pressure is servoed by controlling speed to be equal to inspiratory pressure plus 8 cm $H_2O$. The pressure servo adjusts a speed control servo. The speed control servo is relatively fast in order to maintain a constant speed while the applied loads change rapidly. In contrast, the pressure loop is relatively slow. This combination allows the blower speed to be held substantially constant while still regulating the pressure to be about equal to the desired pressure described above.

Because the inspiratory pressure can range anywhere between 2 and 39 cm $H_2O$, a very slow pressure control loop is not desirable. These conflicting requirements are met by increasing the bandwidth of the pressure control loop 194 by means of the bandwidth (gain) control 191 for large pressure errors. For small errors (which is normal) the bandwidth of the pressure control loop 194 is low. A low loop bandwidth implies a less rapid response. This means that the speed of the blower motor 72 is not changing rapidly, and the noise level is perceived as very low. Large errors occur when the inspiratory pressure is changed. In this case a low bandwidth pressure control loop 194 would be very slow to regulate the pressure to its desired value. The bandwidth of the pressure control loop 194 is therefore increased by means of the bandwidth (gain) control 191 to approach the regulated pressure rapidly. When the actual pressure approaches to the desired pressure, the error is again small, and the bandwidth (gain) control 191 lowers the bandwidth of the pressure control loop 194 again to minimize perceived noise.

As previously discussed, certain prior art pressure support devices have used a blower whose speed is rapidly varied to regulate the output pressure to the patient. Since the output pressure varies somewhat with flow, the blower speed was increased or decreased to maintain patient pressure against the disturbance of patient flow. This changing of speed however, is readily detected as audible noise. If the blower is held at a constant speed, the patient perceives a much lower noise level even though the noise is the same. It is the change of speed that the patient perceives as noise. Accordingly, to minimize noise it was a design goal of the present invention to provide a system wherein the blower runs at substantially constant speed.

Similarly, other prior art pressure support devices run a blower at maximum speed and then vent excess airflow to the ambient. The running of the blower at maximum speed and the venting of the excess airflow to the ambient combine to create an objectionably high noise level. Accordingly it was another design goal of the present invention to minimize noise by requiring the blower to run no faster than is necessary to provide the desired patient pressures and further to minimize noise by employing a novel valve which throttles air, rather than venting it to the ambient.

Having now discussed the various components comprising the pressure support ventilatory assist system 10, the operation of the overall device will now be explained with reference to FIGS. 11A and 11B.

Figure 11A:
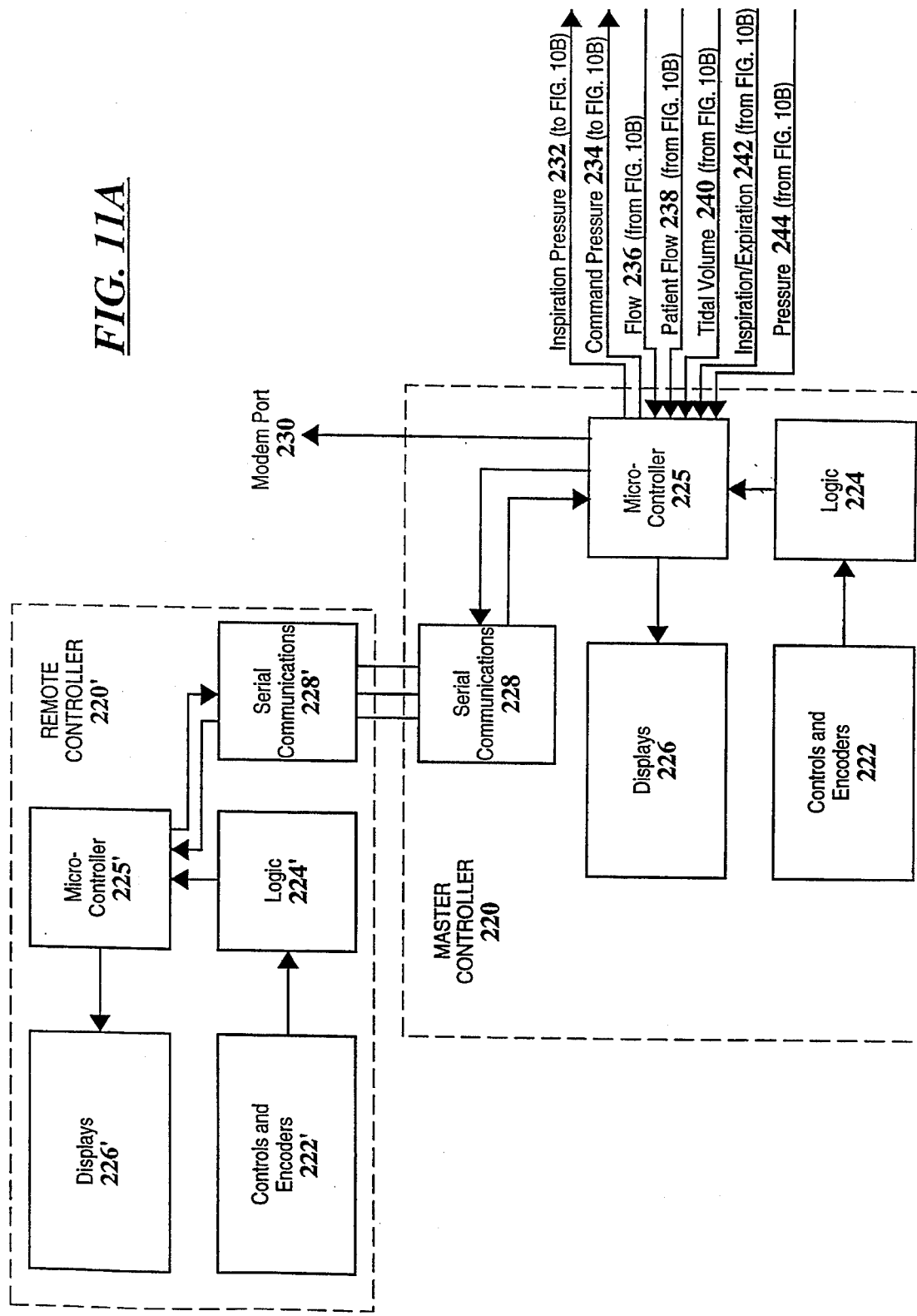
FIGS. 11A and 11B are a block diagram of the pressure support device of the present invention.

Referring first to FIG. 11A, a master controller 220 resides in the main unit 12 of the pressure support device 10. The master controller 220 includes controls and encoders 222. The controls and encoders block 222 includes the control panel 16 shown in FIG. 2, as well as the encoder board 60 and the controls mounted on the display board 58 (refer to FIG. 3). The controls and encoders block communicates with a logic block 224. The logic block, in turn, communicates with a microcontroller 225. The microcontroller 225 controls the displays 226. The displays 226 correspond to those displays on the display board 58 which are visible on the control panel 16 of FIG. 2.

The microcontroller 225 also sends and receives signals with a serial communications block 228, through which the master controller 220 communicates with peripheral devices. In addition, the microcontroller 225 can communicate with a modem through a modem port 230.

FIG. 11A further shows a remote controller 220' which resides on the remote unit 14 of the pressure support device 10 of the present invention. The remote controller 220' includes its own controls and encoders 222', logic board 224', microcontroller 225', and displays 226'. A serial communications block 228' of the remote controller 220' provides an interface by which the remote controller 220' can communicate with the master controller 220.

The microcontroller 225 of the master controller 220 outputs an inspiration pressure 232 and a command pressure 234. The following signals are input into the microcontroller 225: flow 236, patient flow 238, tidal volume 240, inspiration/expiration detect 242, and pressure 244.

Figure 11B:
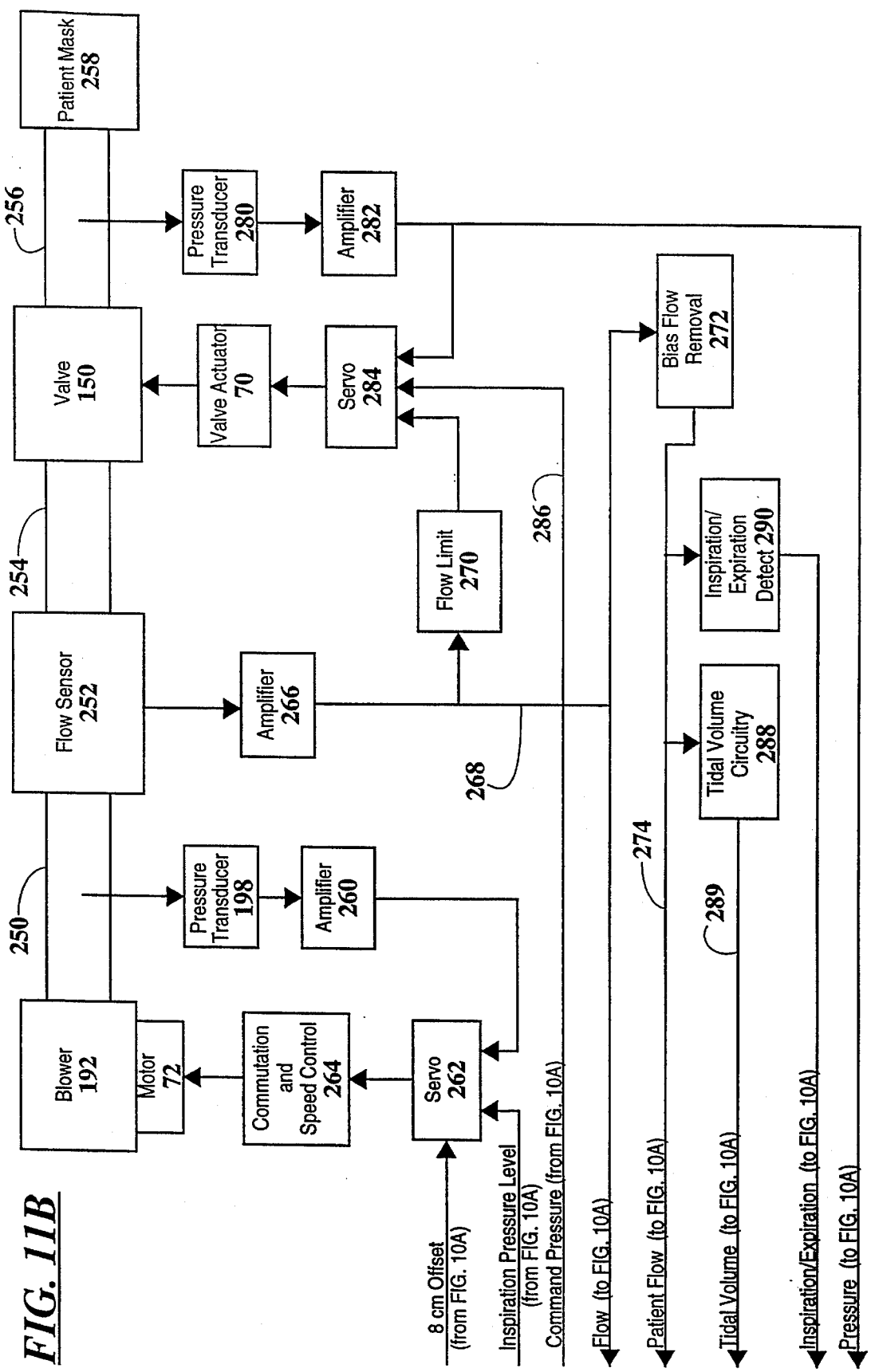

Referring now to FIG. 11B, the blower 192 is driven by the blower motor 72. The blower 192 directs its air flow through a conduit 250 to a flow sensor 252. Air flow exiting the flow sensor 252 moves through a conduit 254 to the inlet side of the valve 150. Air flow exiting the outlet side of the valve 150 travels through a tubing 256 to the patient mask 258.

A pressure transducer, previously assigned the reference numeral 198, is disposed within the conduit 250 between the blower 192 and the flow sensor 252. The pressure transducer 198 produces an output signal representative of the blower pressure. This output signal is amplified by an amplifier 260 and sent to a servo 262. The 8 cm $H_2O$ offset and the inspiratory pressure level are also input into the servo 262, and the output signal from the servo is transmitted to the commutation and speed control circuitry 264. The servo 262 and commutation and speed control circuitry correspond to the motor control block 130 in the block diagram of the control board 56 (FIG. 5).

The flow sensor 252 comprises a differential pressure transducer (not shown) for sensing airflow through the sensor. The differential pressure transducer of the flow sensor 252 generates an output signal which is amplified by an amplifier 266. The output signal from the flow sensor 252 is then input via signal path 268 to the microcontroller 225 (FIG. 11A).

The output signal from the flow sensor 252 is also sent to a flow limit circuit 270. The purpose of the flow limit circuit is to prevent the capacity of the blower 192 from being exceeded. If blower capacity about 3.0 liters/second—were to be exceeded, current limiting circuitry for the blower motor 72 would preclude active speed control, and blower speed would decrease. The decrease in the blower speed would be audibly detectable as objectionable noise. To prevent this possibility, if the airflow through the flow sensor 252 exceeds 3.1 liters/second, the flow limit circuitry 270 operates the valve 150 to attenuate flow, thereby preventing the blower capacity from being exceeded.

The output signal from the flow sensor 252 is also sent to bias flow and leakage removal circuitry 272. For purposes of this discussion, "bias flow" refers to airflow which is intentionally exhausted through a port in the patient mask, and leakage refers to airflow which unintentionally exits around the edges or the patient mask. After the bias flow and leakage circuitry 272 adjusts the sensed airflow to compensate for leaks and bias flow, the resulting signal corresponds to patient flow. The signal corresponding to patient flow is input via signal path 274 to the microprocessor 225 (FIG. 11A).

A pressure transducer 280 is located at the outlet side or the valve 150. An output signal from the pressure transducer 280 is amplified by an amplifier 282 and transmitted to a servo 284. The servo 284 corresponds to the valve control 122 on the control board 56 (FIG. 5). A signal corresponding to the command pressure is output from the microcontroller 225 and input into the servo 284 via signal path 286. The output signal from the flow limit circuitry 270 is also input into the servo 284. In response to these input signals the servo 284 controls the valve actuator 70 to operate the valve 150.

In addition to being input into the microcontroller 225, the output signal from the bias flow and leakage circuitry 272 corresponding to patient flow is also input to tidal volume circuitry 288. The function of the tidal volume circuitry 288 is to calculate the tidal (inspiration) volume from the patient flow. The resulting output signal corresponding to the calculated tidal volume is input into the microcontroller 225 by way of signal path 289.

Finally, the output signal from the bias flow and leakage circuitry 272 corresponding to patient flow is also input to inspiration/expiration detect circuitry 290. The function of the inspiration/expiration detect circuitry 290 is to monitor patient flow and track the onset of patient inspiration and expiration. The resulting output signal corresponding to a detected patient inspiration or expiration, is input via signal path 292 to the microcontroller 225.

The pressure support device 10 of the disclosed embodiment features modes of operation that raise the patient pressure during the patient's natural inspiration and lower it during the subsequent expiration. Various means are available to monitor patient inspiratory effort. Like many ventilator-class devices, the pressure support device 10 of the disclosed embodiment uses the non-intrusive patient air flow method. That is, the pressure support device's inspiration/expiration detector block 290 continuously monitors air flow levels out of the blower 172 into the valve 150. Signal processing techniques separate leak flows from patient flows, set an inspiratory threshold, and generate timing pulses corresponding to the inspiratory and expiratory phases of respiration.

In the architecture of the pressure support ventilator device 10, the flow sensor 252 is located between the blower 192 and the pressure regulator valve 150. Some prior art ventilator devices have located the flow meter between the valve and patient. However, locating the flow sensor between the pressure regulator valve and the patient subjects the flow meter to possible fluids in the patient hose. In addition, the characteristic resistance of the flow meter to a person trying to exhale might be objectionably high. Removing the flow sensor 252 to a location between the blower 192 and the valve 150 avoids these problems.

Figure 12A:
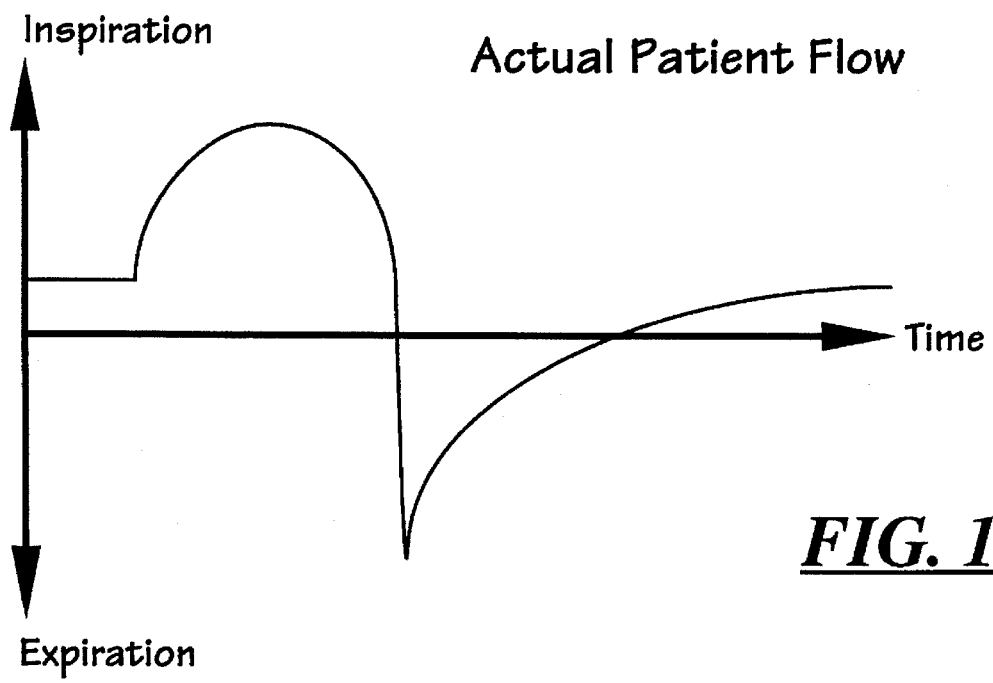
FIG. 12A is a graph showing actual patient flow.
Figure 12B:
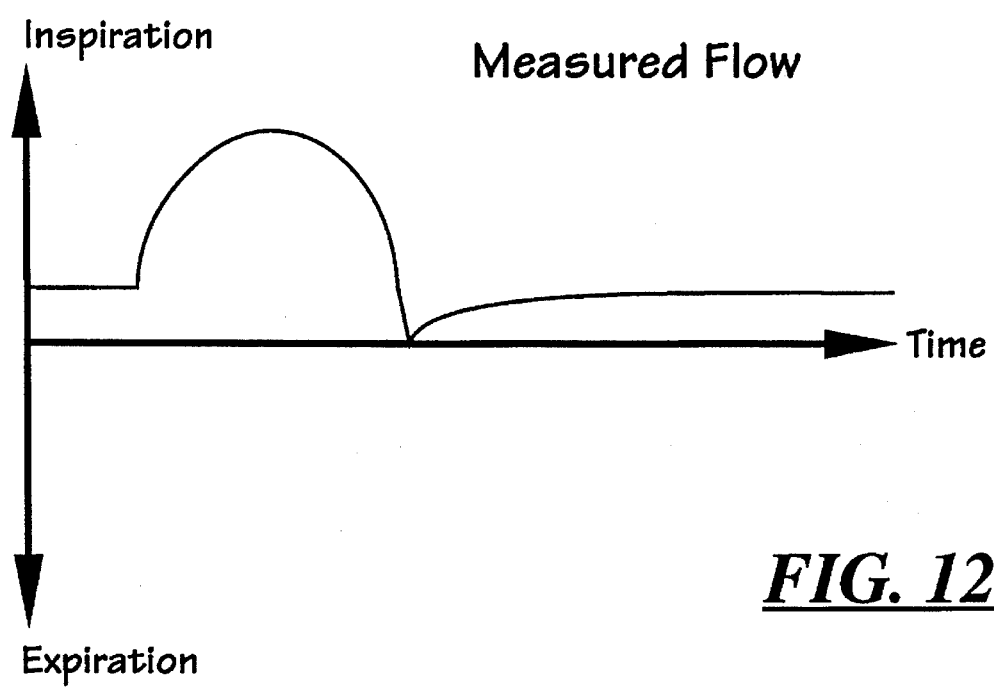
FIG. 12B is a graph showing flow as measured by the flow sensor of the pressure support device of the present invention.

During inspiration, the valve 150 opens enough to elevate the patient pressure to the support level. When the patient is ready to exhale, the flow level decreases, and the valve 150 closes. However, the exhaust ports 162, 164 on the valve 150 simultaneously open to atmosphere, which ensures the lowering of patient pressure to the required level. Because air is dumped overboard, the flow sensor 252 does not see that flow directly. Consequently, as can be seen in FIG. 12, the flow observed by the flow sensor 252 during the patient's expiration is diminutive, compared to the magnitude of the previous observed inspiration.

In these discussions "expiratory waveform" refers to the measured waveform of the flow sensor 252 during the expiration period. Although significantly smaller than normal, the expiratory waveform is still useful. The worst case detection conditions are at low positive end expiratory pressure ("PEEP") levels, where the bias flow leaks are small.

Figure 13A:
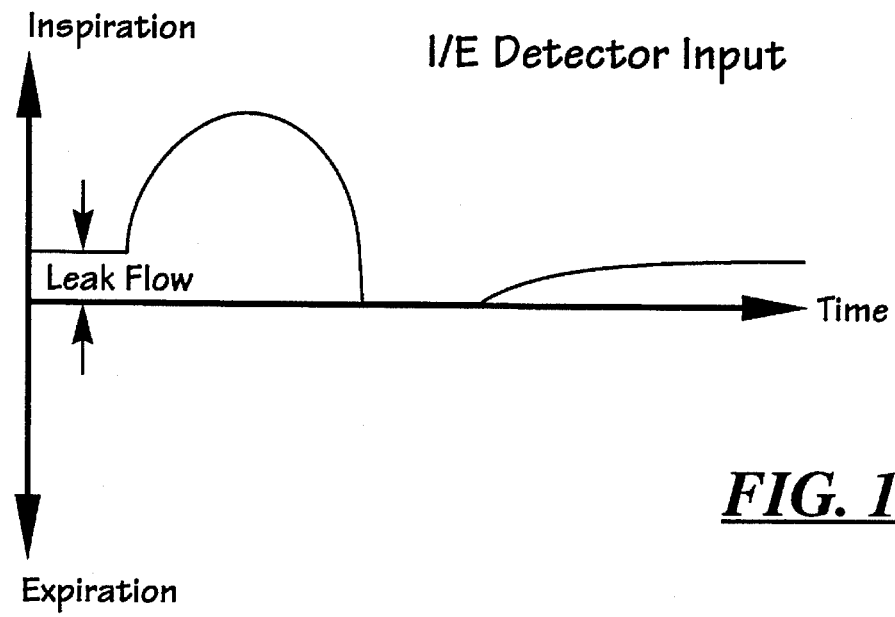
FIG. 13A is a graph representing the airflow sensed by the flow sensor.
Figure 13B:
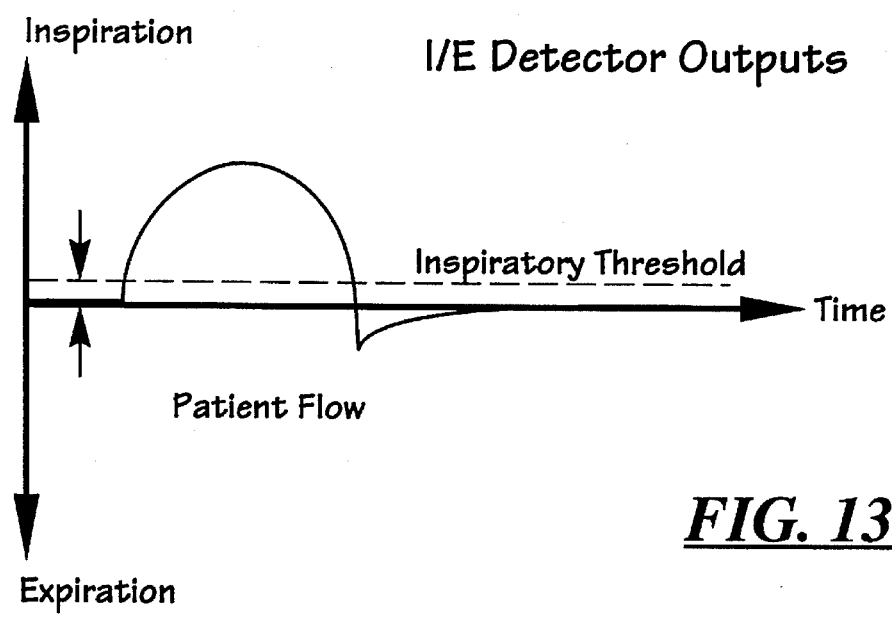
FIG. 13B is a graph representing the patient flow output from the inspiration/expiration circuit.
Figure 13C:
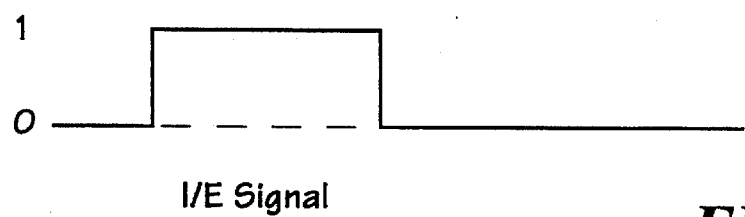
FIG. 13C is a graph representing the resultant I/E signal.

Because the exhaust ports 162, 164 on the valve 150 relieve reverse flow, the flow sensor 252 does not see absolute negative flows. In the waveform shown in FIG. 13A, the negative peak at the start of expiration has been truncated. FIG. 13B shows the patient flow output of the circuit, which has the leak flow component removed. The inspiratory threshold, set at about 0.32 L/s, is shown just above the zero patient flow line. FIG. 13C depicts the resultant I/E signal. When the patient flow waveform exceeds the inspiratory threshold, the I/E signal changes state. In actual circuit implementation, hysteresis causes the threshold to lower slightly once patient flow has risen above the threshold level.

Figure 14A:
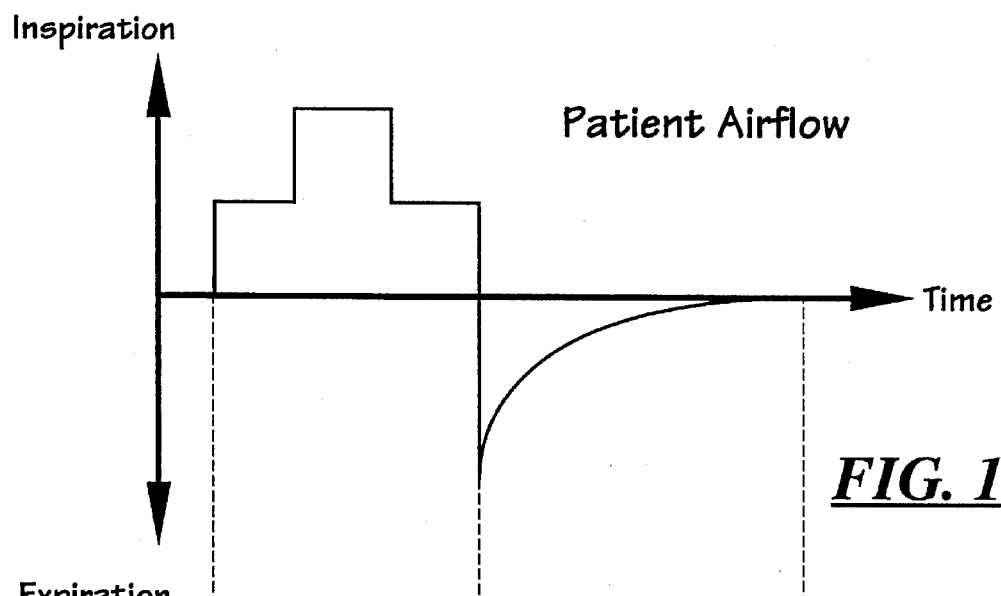
FIG. 14A is a graph representing an arbitrary inspiratory waveform.

The basic principle of the I/E detection circuit is that for a given patient breathing normally, an inspiration is useful in predicting the subsequent expiration, more so than the converse. There is a proportional relationship between the inspiratory length of time and amplitude (volume of air inhaled) and the same parameters for the expiration of the same breath. Using this principle certain expectations can be made for the expiration waveform. During the expiration phase, differences between the expected and actual expiration waveform can be attributed to changes in leak flows. The differences are adjusted out by slowly changing the leak offset value throughout expiration. By making these corrections in real time, a tracking-type loop is formed. The inspired volume is used to form a model of the expected expiration. See FIG. 14A.

Figure 14B:
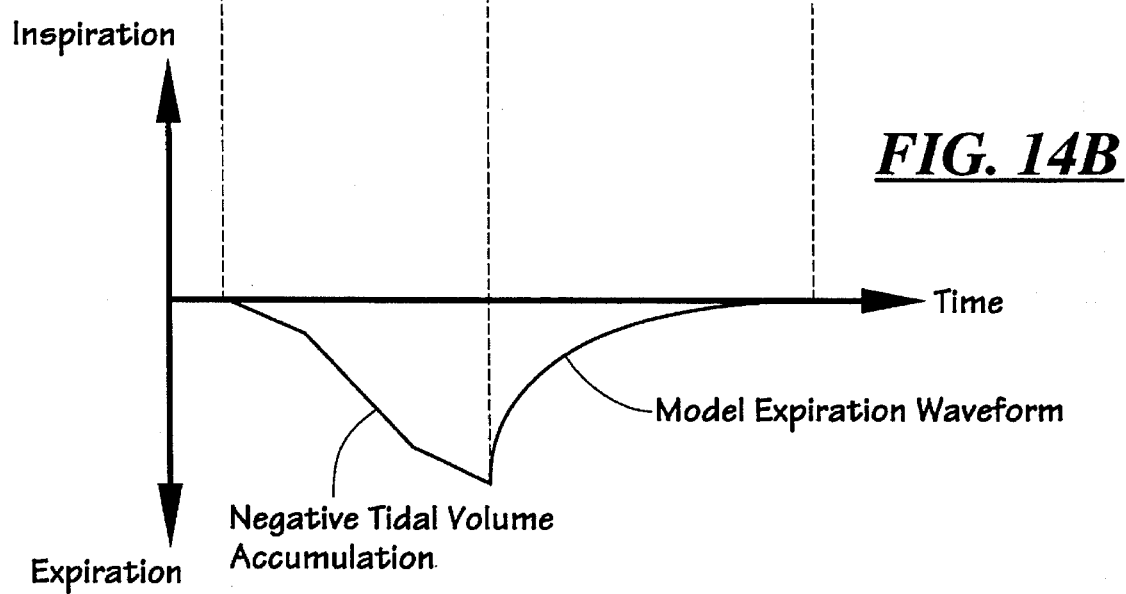
FIG. 14B is a graph representing an expiratory waveform as modeled from the detected inspiration waveform.

During inspiration, the tracking circuit creates a tidal volume (inspired volume) value. Notice in FIG. 14B the arbitrary inspiratory waveform containing two different levels. Below, the tidal volume accumulates in the negative direction. Its varying slopes show how it responds to inspiratory activity. The greater the inspiratory flows, the greater the rate of tidal volume accumulation. In a passive exhalation, humans create a roughly exponential flow waveform. When inspiration ends, the negative tidal volume value is the starting point for its exponential ascent back to zero value.

As previously discussed, the expiration waveform is diminutive in the pressure support device 10 because of the physical location of the flow sensor 252. Yet, the constant bias flow at the mask elevates the total flow waveform to see some expiration activity. In the actual circuit, the expiration model is attenuated from the ideal to match the smaller observed flow levels. In other words, the model has been adapted to see expiration flows as the pressure support ventilator sensor presents them. Though now small, the space between the model and the non-respiratory flow line is valuable area within which to do error correction and null out leaks. Undoubtedly, seeing less of expiration than is actually occurring fundamentally limits that rate of change of leak flows that may be nulled out. However, the tracking strategy can still be effective because the model works both in amplitude and time. The most important aspect of the model is that regardless of initial amplitude it converges to zero, as any exponential model will do.

Figure 15A:
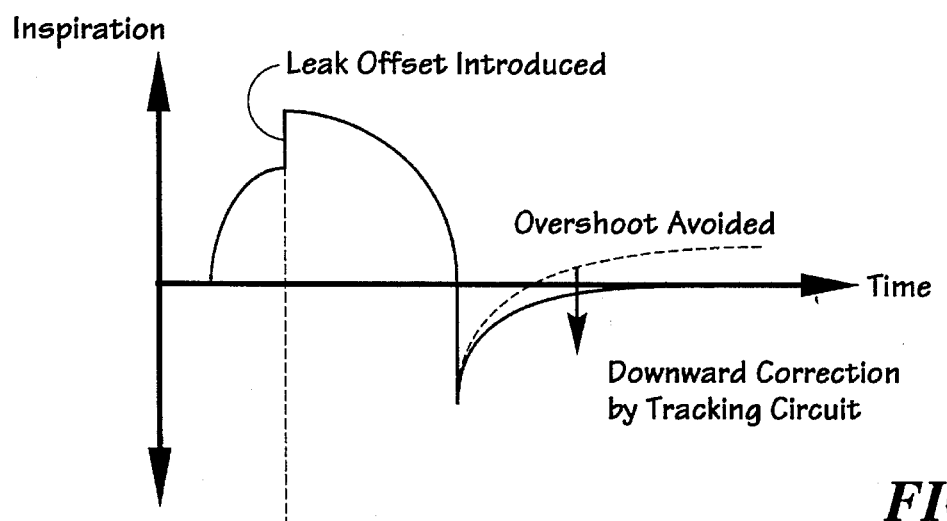
Figure 15B:
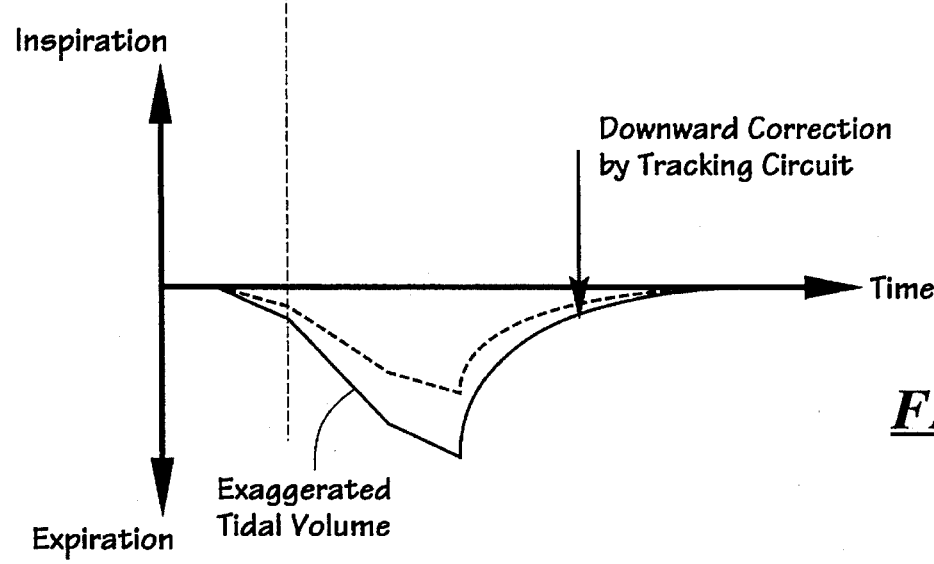
FIG. 15B is a graph showing the effect of tracking circuit corrections on the predicted expiration waveform.

Creating an expiration model that is proportional to the preceding inspiration is a key part of the tracking circuit's ability to null out non-respiratory, or leak, flows. For example, if the patient breathes normally, but an additional leak flow develops during inspiration, the additional positive flows create an exaggerated tidal volume value. As shown in FIGS. 15A and B, the dashed line waveforms are those that would occur if the tracking circuit corrections did not intervene. While expiration activity still pushes the waveform below the inspiratory threshold into expiration, the new positive offset causes the expiration waveform to ascend above the threshold prematurely. However, the exaggerated tidal volume makes the expiration model larger (more negative). The model then applies downward corrections on patient flow (same as increasing leak flow estimate). In this way, the leak is nulled out in early expiration. A false inspiratory trigger is avoided. The correction scenario is similar for a reduction in leak flow.

The respiratory waveform tracking loop necessarily has built-in boundary conditions. That is, invalid or confusing waveforms must be handled gracefully so that tracking can resume whenever normal respiration activity resumes. First, the inspiration period is limited to about four seconds. If the patient flow waveform stays above the inspiratory threshold for more than four seconds, a "reset" timer causes the circuit to declare the present flow level as the new non-respiratory (or, zero) flow. This causes the I/E signal to return to the expiration state. There is no expiration time limit, so expiration may theoretically be infinitely long. This makes expiration as the natural resting state of the tracking circuit.

Figure 16:
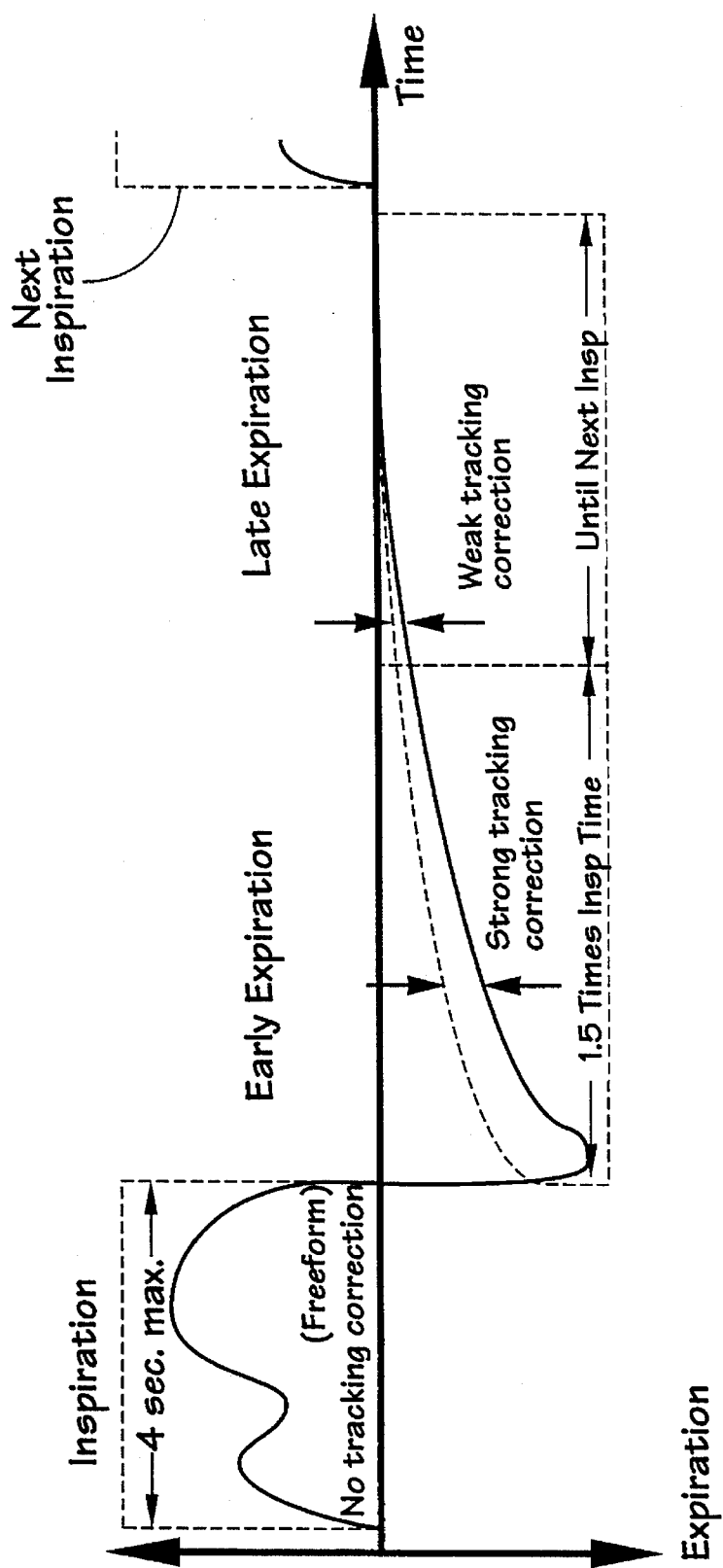
FIG. 16 is a graph showing airflow as a function of time, with the airflow waveform divided into zones with respect to the tracking cycle.

It is useful to understand tracking circuit operation by examining boundary conditions and tracking corrections in terms of "zones". Referring to FIG. 16, the tracking cycle for a single breath consists of (a) inspiration, (b) early expiration, and (c) late expiration. To enter the inspiration zone, the patient flow waveform crosses the inspiratory threshold. During inspiration, no corrections to leak flow are made. An odd-looking inspiratory waveshape is shown in FIG. 16, indicating the flow signal may exhibit any freeform flow, as long as it descends through the inspiration threshold before four seconds passes.

When the expiration phase begins, the tracking circuit begins to make corrections to the estimated leak flow level. These are in effect until the next inspiration begins. The model expiration waveform is synthesized while the actual one progresses. They are compared, and any difference is treated as an error. The leak offset is adjusted on a continuous basis until the difference no longer exists, or until the next inspiration has begun. The expiration phase is divided into two zones: early and late expiration. These are actually a two step linearization of a probability continuum. Stated simply, it is not known precisely when the next inspiration is going to occur. However, the I/E ratio is more typically 1:2, regardless of breath rate. In the time just after expiration begins, it is least probable that a new inspiration will occur. As time passes, it becomes increasingly probable that a new inspiration will occur. Thus tracking errors are multiplied by a larger gain during early expiration, and by a smaller gain during late expiration. It is important to note that when the patient does actually try to start a new breath, the slope of the flow waveform has to outrun the tracking circuit's rate of correction (otherwise, their attempt to inhale into the freeform area of inspiration will be nulled out as leaks). So, by making the strongest leak corrections during early expiration, the error gain is lowered, and sensitivity to shallow breathing (weak inspiratory efforts) is maintained.

The time of inspiration is stored in an analog timer. During expiration, the timer is reversed at a slower rate, 1.5 times the inspiratory time. Its time-out is used to separate early from late expiration. The constant of 1.5 is chosen because it allows early expiration to end before most I/E ratios have the next inspiration begin. If the patient's I/E ratio falls below 3:2 then the late expiration zone will be bypassed as the tracking circuit cycles. This is acceptable, because the usual cause for short expiration periods is when expiration is forced (as in heavy breathing), rather than passive. This results in higher flow signal amplitudes, further enhancing our ability to track.

So far in these discussions the concept of the I/E (Inspiration/Expiration) signal has been simplified to facilitate the introduction of tracking methodology. Now specifically, the I/E detector creates two distinct logic-level "I/E" signals. Each signal goes to the CPU board for use by the microcontroller. As shown in FIGS. 17A–C, the signals are called "I/E Zero Cross" and "I/E 75%". In terms of indicating inspiration activity, both are inverted (low during patient inspiration). Both signals go to the active state when patient flow exceeds the inspiratory threshold. Circuitry ensures the leading edges are aligned. When patient flow returns to the non-respiratory flow level (actually the inspiratory threshold), I/E zero cross is de-asserted (FIG. 17B). The purpose of this signal is for the microprocessor's use in doing patient data calculations. It is for real-time use in discerning inspiration from inspiration. The second signal, "I/E 75%," (FIG. 17C) is used in pressure control. The leading edge tells the waveform generator that it is time to raise the pressure. This aids the patient in inspiration. The trailing edge has a timing "advance" feature. When the inspiratory flow drops to 75% of its peak value, I/E 75% is de-asserted to the expiration state.

Figure 18:
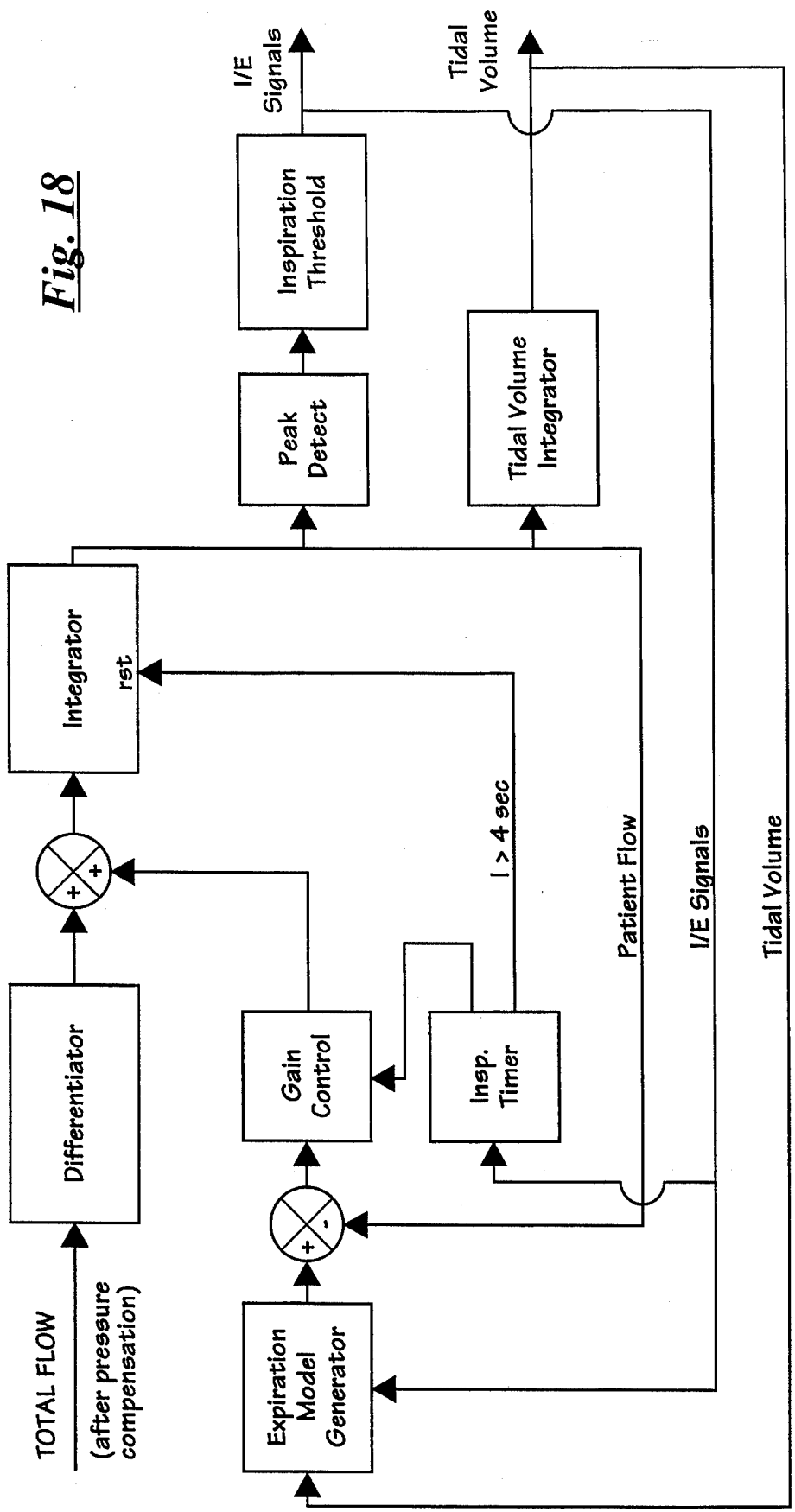
FIG. 18 is a block diagram representing the tracking loop of the pressure support device of the disclosed embodiment.

With these mathematical principles of tracking in mind, implementation of the tracking circuit will now be discussed with reference to FIG. 18.

At the upper left of the diagram, the Total Flow provides the input for respiratory tracking. This point is after the pressure compensation stage for variations in leak flow at the bis port. The differentiator/integrator pair pass the signal straight through, minus the current leak flow offset stored in the integrator. The peak detector and inspiration threshold boxes produce the two I/E signals. The I/E zero cross is used internally in the tracking circuit. It tells the tidal (inspiratory) volume integrator when to integate. The tidal volume output is used externally, but it also goes to the expiration model generator. The I/E signal tells the model when to go into action. Its output and the patient flow signal enter a difference node that feeds a variable gain stage. The inspiration timer controls its gain, depending on whether the phase is inspiration, early expiration, or late expiration. Inspirations that last more than four seconds result in a reset of the integrator, effectively declaring late expiration and setting the current patient flow to zero.

Part of the task of the analog flow signal processing effected by the control board 56 is to provide flow-related patient data to the CPU board 66 for each patient breath cycle. These data include the two analog signals "tidal volume" and "peak inspiratory flow." Both signals are naturally generated as part of the tracking circuit. The waveforms begin by assuming all variables are currently zero, and the first breath after t=0 has now arrived. Patient airflow as a function of time for the patient breath cycle is represented by the graph of FIG. 19A. As shown in FIG. 19B, peak inspiratory flow follows patient flow exactly, and holds the peak value throughout the following expiration. At the beginning of the next inspiration, the peak hold value is reset to zero. It is quickly released in order to track the next inspiration. Similarly, tidal volume (or inspiratory volume) accumulates during inspiration by an integrator function, as shown in FIG. 19C, and its value is held throughout expiration. It is also reset and released upon the detection of the next inspiration. The CPU on the control board uses the I/E zero cross signal to coordinate the reading of valid data from these variables. Immediately after expiration begins, the values are read and displayed on the front panel.

The steps followed by the pressure support device 10 for detecting inspiration can thus be summarized as follows:

(1) At the end of inspiration, a model is generated of predicted expiratory flow based upon the inspired volume of air. The expiratory flow waveform model will converge to zero, but the actual flow will not.

(2) The actual flow is then compared to the model, and the actual flow is modified to conform to the model. Early in the expiratory phase, strong corrections are made to the actual flow. Late in the expiratory phase, weaker corrections are made to the actual flow.

(3) Since corrections are being made to the actual flow to make it ultimately (end expiration) be equal to zero, and since the actual flow will not be zero, the corrections will represent the difference which is leakage flow.

(4) The leakage flow is removed from subsequent flows.

(5) Inspiration is considered to start when the flow less the leakage flow is greater than some small value greater than zero. This small value is chosen to ensure that the system does not prematurely indicate inspiration in the presence of noise.

(6) This process is repeated for every subsequent breath.

The prediction process outlined above does not include considerations to address extreme conditions. These considerations are made by setting limits to the values calculated in the prediction process. These limits are that inspiration may not last more than four seconds and that inspired volume may not exceed five liters. These limits would not generally be imposed because they represent values higher than a human patient could obtain. However, these limits are useful in the case of an error by the predicting circuitry. In that sense the limits constrain the prediction circuitry to the high end of values of actual human respiration.

The pressure support ventilatory assist device 10 of the disclosed embodiment is operable in any of four modes. In the "CPAP" mode, the inspiration pressure and expiration pressure are the same. In the "support" mode, inspiration pressure and expiration pressure are set independently, and the device alternates between the two pressure levels based solely upon detected inspiration/expiration. In the "support/control" mode, inspiration and expiration are set independently, and the device alternates between the two pressure levels based upon detected inspiration/expiration, with the exception that if an inspiration/expiration is not detected within a predetermined time interval, the device will switch to the other pressure level regardless of whether inspiration/expiration is detected. Finally, in "control" mode, inspiration and expiration are set independently, and the device alternates between the two pressure levels based solely upon the passage of predetermined time intervals.

As previously discussed, "rise time," that is, the time it takes for the pressure support device 10 to increase from expiratory pressure to inspiratory pressure, is a significant factor in patient comfort. Further, since the rise time which is "comfortable" will vary from patient to patient, it was a design goal of the disclosed embodiment to provide a means for controlling rise time. In the pressure support device 10 the microprocessor generates a profile for raising the patient pressure from expiration pressure to inspiration pressure within the desired rise time, as set by the operator via the control panel 16. The command pressure output signal generated by the microprocessor follows this profile to drive the pressure control loop to achieve the desired rise time. In addition, "fall time," or the time it takes for pressure to drop from inspiratory pressure to expiratory pressure, is set at 25% of the rise time or 100 milliseconds, whichever is greater. In CPAP mode, since inspiratory pressure is equal to expiratory pressure, rise time and fall time are not applicable.

In the disclosed embodiment the profile generated for increasing the pressure level from expiration pressure to inspiration pressure is an exponential curve. However, it will be appreciated that the invention is by no means limited to an exponential profile but will also be understood to encompass other profiles, including a linear ramp-up or any other suitable profile.

Finally, it will be understood that the preferred embodiment has been disclosed by way of example, and that other modifications may occur to those skilled in the art without departing from the scope and spirit of the appended claims.

What is claimed is:

1. A pressure support ventilatory assist device comprising:

a blower;

a patient mask;

a conduit for placing said blower in fluid communication with said patient mask;

a valve disposed in-line of said conduit between said blower and said patient mask;

a flow sensor disposed between said blower and said valve for measuring airflow within said conduit between said blower and said valve, said measured airflow corresponding to air inspired by a patient plus bias flow and leakage;

inspiration/expiration detection means operatively associated with said flow sensor for detecting the beginning and the end of a patient's inspiration;

modeling means operative upon detection of an end of inspiration by said inspiration/expiration detection means for generating a predicted expiration waveform based upon said measured airflow;

comparator means for comparing actual airflow measured by said flow sensor to said predicted expiration waveform; and valve control means for operating said valve to conform said actual airflow to said predicted expiration waveform.

2. The device of claim 1, further comprising means for computing bias flow and leakage based upon the corrections necessary to conform said actual airflow to said predicted expiration waveform.

3. The device of claim 2, further comprising means for subtracting said computed bias flow and leakage from subsequent breaths.

4. The device of claim 2, wherein said inspiration/expiration detection means identifies the onset of an inspiration when airflow measured by said flow sensor exceeds computed bias flow and leakage.

5. The device of claim 1, further comprising means responsive to a detected onset of patient inspiration for operating said valve to increase pressure in said conduit between said valve and said patient mask.

6. The device of claim 5, further comprising:

timing means for timing the interval between the beginning of an inspiration and the end of said inspiration, and limit means responsive to said timed interval exceeding a predetermined time period for operating said valve to increase pressure in said conduit between said valve and said mask.

* * * * *